(12) United States Patent
Adams et al.

(10) Patent No.: US 6,800,627 B1
(45) Date of Patent: Oct. 5, 2004

(54) PIRAZINO INDOLE DERIVATIVES

(75) Inventors: David Reginald Adams, Winnersh (GB); Jon Mark Bentley, Winnersh (GB); James Davidson, Winnersh (GB); Matthew Alexander James Duncton, Winnersh (GB); Richard Hugh Phillip Porter, Winnersh (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/890,186

(22) PCT Filed: Jan. 28, 2000

(86) PCT No.: PCT/GB00/00244

§ 371 (c)(1),
(2), (4) Date: Oct. 9, 2001

(87) PCT Pub. No.: WO00/44753

PCT Pub. Date: Aug. 3, 2000

(30) Foreign Application Priority Data

Jan. 29, 1999 (GB) ............................................. 9902047

(51) Int. Cl.$^7$ .................... C07D 487/04; A61K 31/495; A61P 3/04
(52) U.S. Cl. ....................................... 514/250; 544/344
(58) Field of Search ........................... 544/344; 514/250

(56) References Cited

U.S. PATENT DOCUMENTS 3,853,878 A * 12/1974 Jonas et al. .................. 260/268
5,854,245 A * 12/1998 Duggan et al. ............. 544/360

FOREIGN PATENT DOCUMENTS

| CA | 2097465 | 12/1993 |
|---|---|---|
| CA | 2132887 | 4/1995 |
| EP | 0 572 863 | 4/1993 |

OTHER PUBLICATIONS

Mokrosz et al., "Structure Activity Relationship Studies of CNS Agents on the Bioactive Conformation of 1–Arylpiperazines Once More," *Medicinal Chemistry Research*, Birkhauser Boston, vol. 3, pp. 240–248, (1993).

* cited by examiner

*Primary Examiner*—Richard L. Raymond
*Assistant Examiner*—Venkatararaman Balasubramanian
(74) *Attorney, Agent, or Firm*—Foley & Lardner LLP

(57) ABSTRACT

Chemical compounds of formula (I):

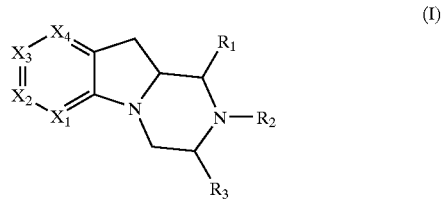

and pharmaceutically acceptable salts and addition compounds and prodrugs thereof are useful in therapy, particularly for the treatment of disorders of the central nervous system; damage to the central nervous system; cardiovascular disorders; gastrointestinal disorders; diabetes inspidus, and sleep apnea.

18 Claims, No Drawings

PIRAZINO INDOLE DERIVATIVES

The present invention relates to pyrazinoindole derivatives, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "Obesity: Trends and Treatments", *Scrip Reports*, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin release/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, *Psychopharmacol.*, 1988, 98, 93–100, G. A. Kennett, C. T. Dourish and G. Curzon, *Eur. J. Pharmacol.*, 1987, 141, 429–453) and to accelerate the appearance of the behavioural satiety sequence (S. J. Kitchener and C. T. Dourish, *Psychopharmacol.*, 1994, 113, 369–377). Recent findings from studies with mCPP in normal human volunteers and obese subjects have also shown decreases in food intake. Thus, a single injection of mCPP decreased food intake in female volunteers (A. E. S. Walsh et al., *Psychopharmacol.*, 1994, 116, 120–122) and decreased the appetite and body weight of obese male and female subject during subchronic treatment for a 14 day period (P. A. Sargeant et al., *Psychopharmacol.*, 1997, 113, 309–312). The anorectic action of mCPP is absent in 5-HT$_{2C}$ receptor knockout mutant mice (L. H. Tecott et al., *Nature*, 1995, 374, 542–546) and is antagonised by the 5-HT$_{2C}$ receptor antagonist SB-242084 in rats (G. A. Kennett et al., *Neuropharmacol.*, 1997, 36, 609–620). It seems therefore that mCPP decreases food intake via an agonist action at the 5-HT$_{2C}$ receptor. However, although both mCPP and TFMPP exhibit high affinity for the 5-HT$_{2C}$ receptor they are both non-selective, having appreciable activity at other 5-HT receptors (G. A. Kennett, *Curr. Opin. Invest. Drugs*, 1993, 2, 317–362).

The preparation of pyrazino[1,2-a]indoles as serotonergic agents, useful as antidepressants and anxiolytics, is disclosed in PCT application WO 9612721. The compounds of this invention are reported to possess high affinity for the serotonergic 5-HT$_{1A}$ receptor. Substituted pyrazino[1,2-a]indoles are used as intermediates in the preparation of heterocyclyl O-substituted alcoholamines as fibrinogen receptor antagonist products as disclosed in PCT application WO 9800401. Pyrazino[1,2-a]indole derivatives are also reported in the preparation of 3-piperazinomethylpyrrolo[2,3-b]pyridines as dopamine D4 receptor antagonists as disclosed in U.S. Pat. No. 5,576,319 and WO 9420497. 1,2,3,4,10,10a-Hexahydropyrazino[1,2-a]indole and 3-ethyl-1,2,3,4,10,10a-hexahydropyrazino[1,2-a]indole are disclosed in *Med. Chem. Res.*, 1993, 3, 240–248 and their 5-HT$_{1A}$ and 5-HT$_2$ binding affinity reported. The 5-HT$_{1A}$ and 5-HT$_2$ binding affinity for 1,2,3,4,10,10a-hexahydropyrazino[1,2-a]indole is reported to be the same as that observed for 1-phenylpiperazine and demonstrates an approximate ten fold selectivity for 5-HT$_{1A}$ receptors.

It is an object of this invention to provide selective, directly acting 5-HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

According to the present invention there is provided a chemical compound of formula (I):

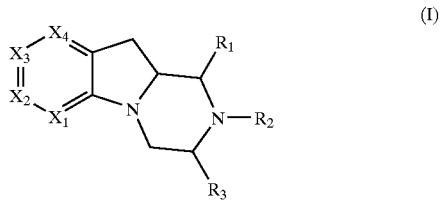

wherein:
R$_1$ to R$_3$ are independently selected from hydrogen and lower alkyl;
X$_1$ is selected from N and C—R$_4$;
X$_2$ is selected from N and C—R$_5$;
X$_3$ is selected from N and C—R$_6$;
X$_4$ is selected from N and C—R$_7$;
R$_4$, R$_5$ and R$_7$ are independently selected from hydrogen, halogen, hydroxy, alkyl, aryl, alkoxy, aryloxy, alkoyl aryloyl, alkylthio, arylthio, alkylsulfoxyl, arylsulfoxyl, alkylsulfonyl, arylsulfonyl, amino, alkylamino, dialkylamino, nitro, cyano, carboalkoxy, carboaryloxy and carboxy; and $R_6$ is selected from hydrogen, halogen, alkyl, aryl, aryloxy, alkylthio, arylthio, alkylsulfoxyl, arylsulfoxyl, alkylsulfonyl, arylsulfonyl, amino, alkylamino, dialkylamino and cyano;

with the proviso that $R_4$ to $R_7$ are not all selected as hydrogen, and pharmaceutically acceptable salts and addition compounds and prodrugs thereof.

As used herein, the term "alkyl" means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl propyl (n-propyl or isopropyl) or butyl (n-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

As used herein the term "aryl" means a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzixazolyl and benzisothiazolyl.

The alkyl and aryl groups may be substituted or unsubstituted. Where substituted, there will generally be 1 to 3 substituents present, preferably 1 substituent. Substituents may include:

carbon-containing groups such as
  alkyl,
  aryl,
  arylalkyl (e.g. substituted and unsubstituted phenyl, substituted and unsubstituted benzyl);
halogen atoms and halogen-containing groups such as
  haloalkyl (e.g. trifluoromethyl);
oxygen-containing groups such as
  alcohols (e.g. hydroxy, hydroxyalkyl, aryl(hydroxy)alkyl),
  ethers (e.g. alkoxy, aryloxy, alkoxyalkyl, aryloxyalkyl),
  aldehydes (e.g. carboxaldehyde),
  ketones (e.g. alkylcarbonyl, alkylcarbonylalkyl arylcarbonyl, arylalkylcarbonyl, arylcarbonylalkyl),
  acids (e.g. carboxy, carboxyalkyl),
  acid derivatives such as esters (e.g. alkoxycarbonyl alkoxycarbonylalkyl, alkylcarbonyloxy, alkylcarbonyloxyalkyl),
  amides (e.g. aminocarbonyl, mono- or di-alkylaminocarbonyl, aminocarbonylalkyl, mono- or di-alkylaminocarbonylalkyl, arylaminocakbonyl),
  carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino);
nitrogen-containing groups such as
  amines (e.g. amino, mono- or di-alkylamino, aminoalkyl, mono- or di-alkylaminoalkyl),
  azides,
  nitriles (e.g. cyano, cyanoalkyl),
  nitro;
sulfur-containing groups such as
  thiols, thioethers, sulfoxides and sulfones
    (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
and heterocyclic groups containing one or more, preferably one, heteroatom,
  (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted there will generally be 1 to 3 substituents present, preferably 1 substituent. Substituents include the substituent groups listed above other than alkyl aryl and arylalkyl.

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine chlorine or bromine radical, and more preferably a fluorine or chlorine radical.

As used herein the term "prodrug" means any pharmaceutically acceptable prodrug of the compound of formula (I) which is metabolised in vivo to a compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, succinic, sulfuric and methanesulfonic acid. Acceptable base salts include alkali metal (e.g. sodium, potassium), alkaline earth metal (e.g. calcium, magnesium) and aluminium salts.

Preferably, $R_1$ is hydrogen or $C_1$–$C_4$ acyclic lower alkyl, preferably hydrogen or saturated $C_1$–$C_4$ acyclic lower alkyl, preferably hydrogen or methyl. In one embodiment of the invention, $R_1$ is hydrogen.

Preferably, $R_2$ is hydrogen or $C_1$–$C_4$ acyclic lower alkyl, preferably hydrogen or saturated $C_1$–$C_4$ acyclic lower alkyl, preferably hydrogen or methyl, more preferably hydrogen.

Preferably, $R_3$ is hydrogen or $C_1$–$C_4$ acyclic lower alkyl, preferably hydrogen or saturated $C_1$–$C_4$ acyclic lower alkyl preferably hydrogen or methyl. In one embodiment of the invention, $R_3$ is hydrogen.

In one embodiment of the invention, $R_1$ and $R_3$ are indepently selected from hydrogen and lower alkyl preferably hydrogen and methyl, and $R_2$ is hydrogen. In a further embodiment, $R_1$, $R_2$ and $R_3$ are hydrogen.

Preferably, $X_1$ is C—$R_4$.
Preferably, $X_2$ is C—$R_5$.
Preferably, $X_3$ is C—$R_6$.
Preferably, $X_4$ is C—$R_7$.

In one embodiment, only one of $X_1$ to $X_4$ is nitrogen. In this embodiment, preferably $X_1$ is N, $X_2$ is C—$R_5$, $X_3$ is C—$R_6$ and $X_4$ is C-$R_7$.

$R_4$, $R_5$ and $R_7$ are independently selected from hydrogen, halogen, hydroxy, alkyl (including cycloalkyl halo-alkyl (such as trifluoromethyl) and arylalkyl), aryl alkoxy (including arylalkoxy), aryloxy, alkoyl, aryloyl, alkylthio, arylthio, alkylsulfoxyl, arylsulfoxyl, alkylsulfonyl, arylsulfonyl, amino, alkylamino, dialkylamino, nitro, cyano, carboalkoxy, carboryloxy and carboxy.

Preferably, $R_4$ is selected from hydrogen and halogen. Preferably, $R_4$ is hydrogen.

Preferably $R_5$ is selected from hydrogen, halogen, alkyl (including cycloalkyl, halo-alkyl (such as trifluoromethyl) and arylalkyl), aryl, aryloxy, alkylthio, arylthio, alkylsulfoxyl, arylsulfoxyl alkylsulfonyl arylsulfonyl, amino, alkylamino, dialkylamino and cyano. In one embodiment, $R_5$ is selected from halogen, halo alkyl (such as trifluoromethyl) and alkylthio, preferably from halogen and alkylthio, and preferably from halogen.

$R_6$ is selected from hydrogen, halogen, alkyl (including cycloalkyl, halo-alkyl (such as trifluoromethyl) and arylalkyl), aryl, aryloxy, alkylthio, arylthio, alkylsulfoxyl, arylsulfoxyl, alkylsulfonyl, arylsulfonyl, amino, alkylamino, dialkylamino and cyano. In one embodiment, $R_6$ is selected from hydrogen, lower alkyl and halogen, preferably from hydrogen and loweralkyl, and more preferably from hydrogen.

Preferably, $R_7$ is selected from hydrogen and halogen, preferably from halogen.

In one embodiment, $R_5$ and $R_6$ are independently selected from hydrogen, chlorine, fluorine, haloalkyl (such as trifluoromethyl) and bromine. In this embodiment, preferably, at least one of $R_5$ and $R_6$, preferably $R_5$, is selected from chlorine, fluorine, haloalkyl (such as trifluoromethyl) and bromine.

In one embodiment of the invention, three of $R_4$ to $R_7$ are hydrogen. In this embodiment, preferably at least $R_4$ and $R_6$ are hydrogen, and more preferably $R_4$, $R_6$ and $R_7$ are hydrogen.

In the embodiment where $R_4$, $R_6$ and $R_7$ are hydrogen and $R_5$ is a substituent group other than hydrogen the preferred stereochemistry at the 10a position is R and, where $R_3$ is alkyl, the preferred stereochemistry at the 3 position is S.

In a further embodiment of the invention, two of $R_4$ to $R_7$ are hydrogen. In this embodiment, preferably at least $R_4$ is hydrogen, more preferably $R_4$ and $R_5$ or $R_4$ and $R_7$ or $R_4$ and $R_6$ are hydrogen, and most preferably $R_4$ and $R_6$ are hydrogen.

In a preferred embodiment, the compounds of the present invention are selected from (RS) 7-chloro-1,2,3,4,10,10a-hexahydropyrazino[1,2-a]indole, (RS) 9-chloro-1,2,3,4,10, 10a-hexahydropyrazino[1,2-a]indole, (RS) 7-chloro-8-methyl-1,2,3,4,10,10a-hexahydropyrazino[1,2-a]indole, (10aR) 7-chloro-1,2,3,4,10,10a-hexahydropyrazino[1,2-a] indole, (RS) 7-bromo-1,2,3,4,10,10a-hexahydropyrazino[1, 2-a]indole and (3S, 10aR) 8-chloro-2-methyl-1,2,3,4,10, 10a-hexahydropyrazino[1,2-a]indole, and particularly from (10aR) 8-chloro-1,2,3,4,10,10a-hexahydropyrazino[1,2-a] indole and (3S, 10aR) 8-chloro-2-methyl-1,2,3,4,10,10a-hexahydropyrazino[1,2-a]indole. In one embodiment, the compounds are in the form of the hydrochloride salt.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis.

According to a further aspect of the invention, there is provided a compound of formula (I) for use in therapy.

The compounds of formula (I) may be used in the treatment (including prophylactic treatment) of disorders associated with 5-$HT_2$ receptor function The compounds may act as receptor agonists or antagonists. Preferably, the compounds may be used in the treatment (including prophylactic treatment) of disorders associated with 5-$HT_{2B}$ and/or 5-$HT_{2C}$ receptor function. Preferably, the compounds may be used in the treatment (including prophylactic treatment) of disorders where a 5$HT_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity.

According to a further aspect of the invention, there is provided a method of treating a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I).

Compounds of the invention may be prepared by conventional methods as illustrated in the Reaction Schemes. $R_1$ to $R_7$ and $X_1$ to $X_4$ are as previously defined.

Reaction Scheme 1

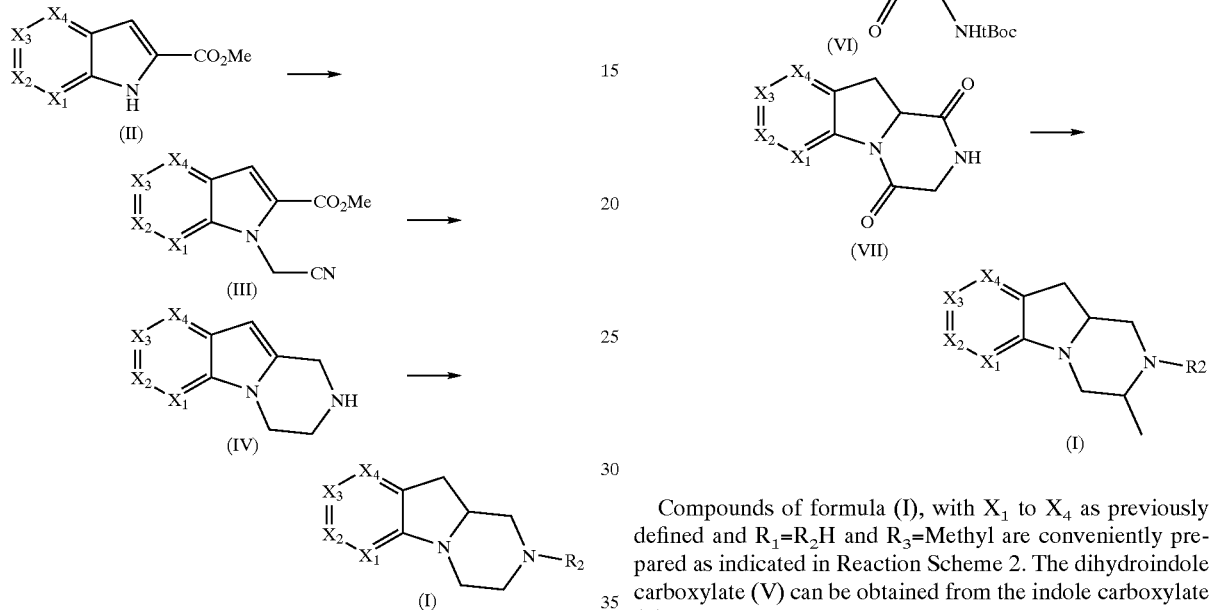

Compounds of formula (I), with $X_1$ to $X_4$ as previously defined and $R_1=R=R_3=H$ are conveniently prepared as indicated in Reaction Scheme 1. The methyl 1-(cyanomethyl) indole-2-carboxylate (III) can be obtained through reaction of the sodium salt of indole carboxylate (II), prepared through treatment of (II) with a base such as sodium hydride in a solvent such as dimethylformamide with a cyanomethylation agent such as chloroacetonitrile. Reduction of (III) to the tetrahydropyrazino[1,2-a]indole (IV) may be achieved with a reducing agent such as lithium aluminium hydride in a suitable solvent such as ether. A compound of formula (I) can the be obtained by the subsequent reduction of the tetrahydropyrazinol[1,2-a]indole (IV) with a reducing agent such as sodium cyanoborohydride in a suitable solvent such as acetic acid.

Compounds of formula (I), with $X_1$ to $X_4$ as previously defined and $R_1=R_3=H$ and $R_2=$loweralkyl are conveniently prepared by standard methods such as reductive alkylation with an appropriate aldehyde or ketone in the presence of a reducing agent such as sodiumtriacetoxyborohydride, formic acid or sodium cyanoborohydride.

Reaction Scheme 2

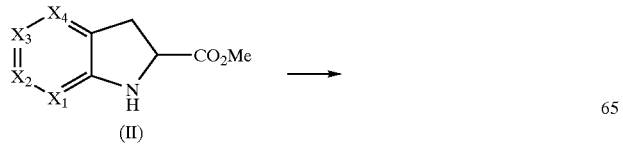

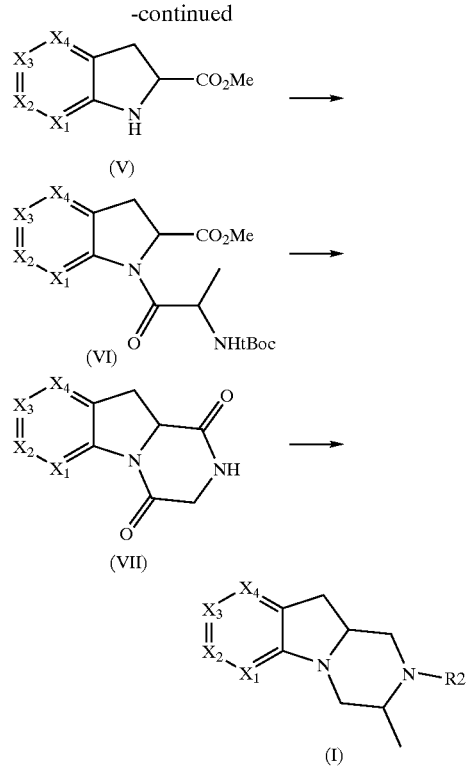

Compounds of formula (I), with $X_1$ to $X_4$ as previously defined and $R_1=R_2H$ and $R_3=$Methyl are conveniently prepared as indicated in Reaction Scheme 2. The dihydroindole carboxylate (V) can be obtained from the indole carboxylate (II) through reduction with a reducing agent such as magnesium in methanol. The dihydro indole alanine ester derivative (VI) can be prepared by treatment of the dihydroindole (V) with a suitably protected alanine derivative such as BOC-alanine in the presence of a coupling agent such as dicyclohexylcarbodiimide (DCC) in a suitable solvent such as dichloromethane. The pyrazino[1,2-a]indole-1,4-dione derivative (VII) can subsequently be prepared by sequential treatment of (VI) with an acid such as hydrogen chloride in methanol followed by a base such as ammonia in methanol. Compounds of formula (I) can then be obtained by reduction of (VII) with a suitable reducing agent such as lithium aluminium hydride in a solvent such as tetrahydrofuran.

Compounds of formula (I), with $X_1$ to $X_4$ as previously defined and $R_1=R_3=H$ and $R_2=$lower alkyl are conveniently prepared by standard methods such as reductive alkylation with an appropriate aldehyde or ketone in the present of a reducing agent such as sodium triacetoxyborohydride, formic acid or sodium cyanoborohydride.

Reaction Scheme 3

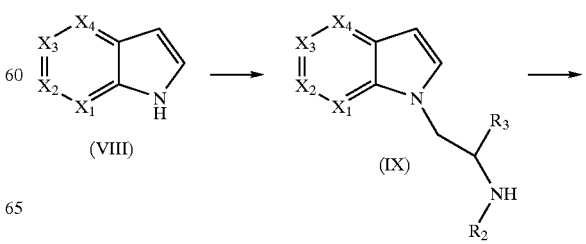

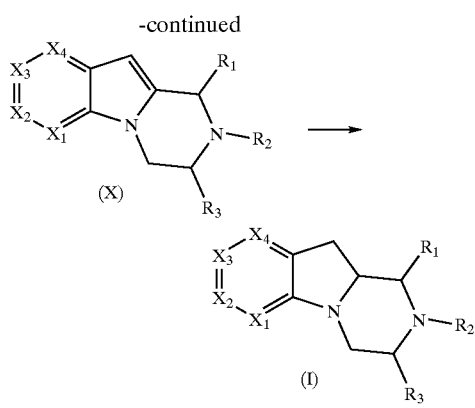

Compounds of formula (I), with $X_1$ to $X_4$ as previously defined are conveniently prepared according to Reaction Scheme 3 (above). The indole-ethylamine (IX) can be obtained by alkylation of the indole (VIII) using, for example, chloroethylamine and a base such as sodium hydroxide in a solvent such as acetonitrile or dichloromethane in the presence of a phase-transfer catalyst The tetrahydropyrazino[1,2-a]indole (X) can be prepared in a two-step procedure from the indole-ethylamine (IX) by treatment with an aldehyde such as formaldehyde followed by exposure to an acid such as trifluoroacetic acid. A compound of formula (I) can then be obtained by reduction of the tetrahydropyrazino[1,2-a]indole (X) using a reducing agent such as sodium cyanoborohydride in a solvent such as acetic acid.

Compounds of formula (I) where $R_2$=loweralkyl may conveniently be prepared from compounds of formula (I) where $R_2$=H using standard methods such as reductive alkylation with an aldehyde or ketone in the presence of a reducing agent such as sodium triacetoxyborohydride, formic acid or sodium cyanoborohydride.

If, in any of the other processes mentioned herein, the substituent group $R_4$, $R_5$, $R_6$ or $R_7$ is other than the one required, the substituent group may be converted to the desired substituent by known methods. The substituents $R_4$, $R_5$, $R_6$ or $R_7$ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

According to a further aspect of the invention, there is provided a process for the preparation of a compound of formula (I) comprising the steps of
 (i) treating a compound of formula (IX) as described herein with an aldehyde and then exposing to acid to obtain a compound of formula (X) as described herein, and
 (ii) reduction of a compound of formula (X).

The reagents used to effect steps (i) to (ii) may be those described with reference to the corresponding steps in Reaction Scheme 3 herein. In a preferred embodiment of this aspect of the invention, the compound of formula (IX) is an indole-ethylamine and the compound of formula (X) is a tetrahydropyrazino[1,2-a]indole.

According to a further aspect of the invention there is provided a process for the production of a compound of formula (X) as described herein comprising the steps of treating a compound of formula (IX) as described herein with an aldehyde and then exposing to acid. The aldehyde may be formaldehyde. The acid may be trifluoroacetic acid. In a preferred embodiment, the compound of formula (IX) is an indole-ethylamine and the compound of formula (X) is a tetrahydropyrazino[1,2-a]indole.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insulation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A suitable dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures

1. Binding to Serotonin Recept rs

The binding of compounds of formula (I) to serotonin receptors was determined in vitro by standard methods. The preparations were investigated in accordance with the assays given hereinafter.

Method (a): For the binding to the $5\text{-}HT_{2C}$ receptor the $5\text{-}HT_{2C}$ receptors ere radiolabelled with $[^3H]\text{-}5\text{-}HT$. The affinity of the compounds for $5\text{-}HT_{2C}$ receptors in a CHO cell line was determined according to the procedure of D. Hoyer, G. Engel and H. O. Kalin, *European J. Pharmacol.*, 1985, 118, 13–23.

Method (b): For the binding to the $5\text{-}HT_{2B}$ receptor the $5\text{-}HT_{2B}$ receptors were radiolabelled with $[^3H]\text{-}HT$. The affinity of the compounds for human $5\text{-}HT_{2B}$ receptors in a CHO cell line was determined according to the procedure of K. Schmuck, C. Ullmer, P. Engels and H. Lubbert, *FEBS Leit.*, 1994, 342, 85–90.

Method (c): For the binding to the $5\text{-}HT_{2A}$ receptor the $5\text{-}HT_{2A}$ receptors were radiolabelled with $[^{125}I]\text{-}DOI$. The affinity of the compounds for $5\text{-}RT_{2A}$ receptors in a CHO cell line was determined according to the procedure of D. J. McKenna and S. J. Peroutka, *J. Neurosci.*, 1989, 9/10, 3482–90.

The thus determined activity of the compound of Example 1 is shown in Table 1.

TABLE 1

| Compound | Method (a) $K_1$ (2C) | Method (b) $K_1$ (2B) | Method (c) $K_1$ (2A) |
| --- | --- | --- | --- |
| Example 1 | 31 | 32 | 53 |

2. Functional Activity

The functional activity of compounds of formula (I) was assayed using a Fluorimetric Imaging Plate reader (FLIPR): CHO cells expressing either the $h5\text{-}HT_{2C}$ or $h5\text{-}HT_{2A}$ receptors were counted and plated into standard 96 well microtitre plates before the day of testing to give a confluent monolayer. The following day the cells were dye loaded with the calcium sensitive dye Fluo 3-AM by incubation with serum free culture maintenance media containing pluronic acid and Fluo 3-AM dissolved in DMSO at 37° C. in a $CO_2$ incubator at 95% humidity for approximately 90 minutes. Unincorporated dye was removed by washing with Hanks balanced salt solution containing 20 mM HEPES and 2.5 mM probenecid (the assay buffer) using an automated cell washer to leave a total volume of 100 µl/well.

The drug (dissolved in 50 µl of assay buffer) was added at a rate of 70 µl/sec to each well of the FLIPR 96 well plate during fluorescence measurements. The measurements are taken at 1 sec intervals and the maximum fluorescent signal was measured (approx 10–15 secs after drug addition) and compared with the response produced by 10 µM 5-HT (defined as 100%) to which it is expressed as a percentage response (relative efficacy). Dose response curves were constructed using Graphpad Prism (Graph Software Inc.).

The thus determined activity of the compounds is shown in Table 2.

TABLE 2

| | $h5\text{-}HT_{2C}$ | | $h5\text{-}HT_{2A}$ | |
| --- | --- | --- | --- | --- |
| Compound | $EC_{50}$ (nM) | Relative Efficacy (%) | $EC_{50}$ (nM) | Relative Efficacy (%) |
| Example 1 | 18 | 91 | 513 | 53 |
| Example 2 | 162 | 84 | 667 | 88 |
| Example 3 | 141 | 82 | 1017 | 49 |
| Example 4 | 13 | 100 | 244 | 58 |
| Example 5 | 20 | 93 | 110 | 87 |
| Example 6 | 174 | 100 | 1678 | 47 |
| Example 7 | 161 | 86 | 144 | 67 |
| Example 8 | 3 | 87 | 100 | 59 |
| Example 11 | 58 | 92 | 527 | 38 |
| Example 12 | 22 | 92 | 106 | 74 |
| Example 13 | 86 | 87 | 176 | 59 |

3. Efficacy

The efficacy of $5\text{-}HT_{2C}$ agonists was assessed for ability to induce a specific syndrome.

The $5\text{-}HT_{2C}$ syndrome is a rapid screening method to assess the in vivo efficacy of $5\text{-}HT_{2C}$ agonists through their ability to induce three specific behaviours in rats. The animals are dosed with either a positive control (mCPP), test compound or vehicle, either s.c. or p.o. The animals are observed on an open bench, typically 30, 60 and 180 minutes and the degree of syndrome is assessed over a two minute period on a scale of 0–3 depending on the presence and severity of splayed limbs, hunched posture and retropulsion, the three specific behaviours which constitute the syndrome. Data is analysed using Kruskal-Wallis Analysis of Variance followed with appropriate post-hoc tests. All statistical analysis are conducted using Excel version 7.0 (Microsoft Corp.) and Statistica version 5.0 (Stasoft, Inc.).

The thus determined activity of Example 1 indicated that after a dose of 1 mg/kg s.c. the compound maintains a significant pharmacological efficacy for at least 180 minutes.

4. Regulation of Feeding Behaviour

The in vivo activity of compounds of formula (I) was assayed for ability to regulate feeding behaviour by assaying food consumption in food deprived animals as follows.

Test compounds are assessed following acute administration. Each study utilises a between-subjects design (typically n=8) and compares the effects of doses of the test agent to those of vehicle and a positive control.

The anorectic drug d-fenfluramine normally serves as a positive control. The route of drug administration, drug volume and injection-test-interval are dependent upon the compounds used. A palatable wet mash, made by adding powdered lab chow and water in a ratio of 1:2 and mixing to a smooth consistency, is presented in 120 mL glass jars for 60 minutes each day. Intake is measured by weighing before and after each session. Care is taken to collect all spillage. Animals are allowed to habituate to the wet mash meal for 10 days. After drug administration, animals are allowed to consume the wet mash. Food consumption is assayed at predetermined time points (typically 1, 2 and 4 hours after administration). Food intake data are subjected to one-way analysis of variance (ANOVA) with drug as a between-subjects factor. A significant main effect is followed up by the performance of Dunnett's test in order to assess which treatment mean(s) are significantly different from the control mean. All statistical analyses were performed using Statistica Software, Version 5.0 (Statsoft Inc.) and Microsoft Excel 7.0 (Microsoft Corp.).

The thus determined activity of Example 1 indicated that the compound maintains significant hypophagia 3 hours after a dose of 1 mg/kg s.c.

SYNTHETIC EXAMPLES

Example 1:

(RS) 7-Chloro-1,2,3,4,10,10a-hexahydropyrazino[1,2-a]indole hydrochloride

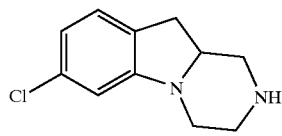

Methyl 6-chloro-1-cyanomethyl)-indole-2-carboxylate

To a stirred solution of methyl 6-chloroindole-2-carboxylate (9.8 g, 46.7 mmol) (D. Knittel, *Synthesis*, 1985, 2, 186–188) in DMF (80 mL) under Ar at ambient temperature was added sodium hydride (60%; 2.80 g, 70 mmol) portionwise over 10 min. After 30 min, chloroacetonitrile (5.9 mL, 93.2 mmol) was added dropwise and the resultant mixture was heated at 75° C. (bath temp.) for 45 min, then allowed to cool. The reaction mixture was poured onto ice (500 mL) and the solid product was filtered, washed with ice-cold water (100 mL), and triturated with refluxing ethanol (150 mL). After allowing to cool to ambient temperature, then cooling in ice, the solid product was filtered-off and washed with ice-cold ethanol (50 mL) to afford the title compound (9.49 g, 82%) as a light grey solid: mp 177–8° C.; IR $\nu_{max}$ (Nujol)/cm$^{-1}$; 3094, 2955, 2925, 2854, 1713, 1613, 1568, 1527, 1519, 1448, 1421, 1398, 1378, 1336, 1306, 1260, 1150, 1108, 1060, 943, 908, 834, 802, 761, 737, 682, 618, 597, 518 and 478; NMR $\delta_H$ (400 MHz, DMSO-d$_6$) 3.95 (3H, s), 5.56 (2H, s), 7.22 (1H, dd, J 8.5, 2 Hz), 7.34 (1H, d, J 1 Hz), 7.43 (1H, br s) and 7.62 (1H, d, J 8.5 Hz).

7-Chloro-1,2,3,4-tetrahydropyrazino[1,2-a]indole fumarate

To a stirred suspension of lithium aluminium hydride (95%; 1.18 g, 29.5 mmol) in anhydrous ether (150 mL) under Ar at 14° C. was added portionwise, over 20 min, methyl 6-chloro-1-(cyanomethyl)-indole-2-carboxylate (2.95 g, 11.9 mmol), allowing the internal temperature to stay at, or below 25° C. After addition was complete, the mixture was heated at reflux for 18 h, then allowed to cool. Water (1.18 mL) was cautiously added, followed by 15% aqueous sodium hydroxide (1.18 mL), then water (3.5 mL). After stirring for 30 min, magnesium sulfate was added and the mixture was filtered through Kieselguhr and washed through with ether (50 mL). The solvent was removed in vacuo and the residue was purified by flash chromatography [SiO$_2$; ethyl acetate-methanol (9:1)] to afford the free-base of the title compound (1.38 g, 56%) as a pale yellow solid: NMR $\delta_H$ (400 MHz, CDCl$_3$) 1.64 (1H, br s), 3.35 (2H, t, J 5.5 Hz), 3.96 (2H, t, J 5.5 Hz), 4.19 (2H, d, J 1.0 Hz), 6.16 (1H, d, J 1.0 Hz). 7.04–7.08 (1H, m), 7.23–7.26 (1H, m), and 7.43 (1H, d, J 8.5 Hz). To a sample of the free-base (130 mg, 0.63 mmol) in 2-propanol (4 mL) was added fumaric acid (110 mg, 0.95 mmol) and the mixture was heated to reflux for 1 min. The resultant suspension was allowed to cool to ambient temperature, and then cooled in ice. The solid was filtered and washed with ice-cold 2-propanol (3 mL) to afford the title compound (184 mg, 90%) as a pale yellow solid: mp 202.5° C. (dec.); NMR $\delta_H$ (400 MHz, DMSO-d$_6$) 3.26 (2H, t, J 5.5 Hz), 4.01 (2H t, J 5.5), 4.12 (2H, s), 7.01 (1H, dd, J 8.0, 2.0 Hz) and 7.45–7.49 (2H, m); Found: C, 55.90; H, 4.72; N, 8.58%. C$_{15}$H$_{15}$ClN$_2$O$_4$ requires C, 55.82; H. 4.68; N, 8.68%.

(RS) 7-Chloro-1,2,3,4,10,10a-hexahydropyrazino[1,2-a]indole

To a stirred solution of 7-chloro-1,2,3,4-tetrahydropyrazino[1,2-a]indole (1.185 g, 5.73 mmol) in acetic acid (40 mL) under Ar at 10° C. was added portionwise over 5 min sodium cyanoborohydride (1.19 g, 18.94 mmol). The resultant mixture was allowed to warm to ambient temperature, and was stirred for 24 h. The mixture was poured into water (200 mL) and was basified (pH 8–9) by the careful addition, with cooling, of ammonium hydroxide (60 mL) over 5 min. The basified mixture was extracted with chloroform (3×200 mL), the combined organic extracts washed with brine (200 mL), dried (magnesium sulfate), and concentrated in vacuo. The residue was purified by flash chromatography [SiO$_2$; ethyl acetate-methanol-ammonium hydroxide (90:8:2)] to afford the title compound (768 mg, 64%) as a colourless oil: NMR $\delta_H$ (400 MHz, CDCl$_3$) 1.60 (1H, br s), 2.50 (1H, ddd, J 15.1, 9.0, 1.0 Hz), 2.74 (1H, dd, J 11.5, 10.5 Hz), 2.79–2.99 (4H, m), 3.04 (1H, dd, J 11.5, 3.5 Hz), 3.42–3.52 (2H, m), 6.37 (1H, d, J 2.0 Hz), 6.57 (1H, dd, J 7.5, 2.0 Hz) and 6.92–6.96 (1H, m).

(RS) 7-Chloro-1,2,3,4,10,10a-hexahydropyrazino[1,2-a]indole hydrochloride

To a solution of 7-chloro-1,2,3,4,10,10a-hexahydropyrazino[1,2-a]indole (747 mg, 3.58 mmol) in acetone (4 mL) was added an ethereal solution of HCl (1 M; 10.75 mL, 10.75 mmol) followed by ether (4 mL). The resultant solid was filtered and washed with ice-cold ether (10 mL) to afford the product (850 mg, 97%) as a white solid: mp 235° C. (dec.); NMR $\delta_H$ (400 MHz, DMSO-d$_6$) 2.59 (1H, dd, J 15.5, 7.0 Hz), 2.83 (1H, t, J 12 Hz), 286–2.95 (1H, m), 3.01 (1H, dd, J 15.5, 8.0 Hz), 3.15–3.36 (4H, m), 3.80–3.90 (2H, m), 6.65 (1H, dd, J 7.5,2 Hz), 6.70 (1H, d, J 2 Hz), 7.08 (1H, d, J 7.5 Hz) and 9.45 (2H, br s); Found: C, 53.88; H. 5.90; N, 11.26% C$_{11}$H$_{14}$Cl$_2$N$_2$ requires: C, 53.89; H, 5.76; N, 11.42%.

The compound of Example 1 may also be described as 8-chloro,1,2,3,4,4a,5-hexahydropyrazino[1,2-a]indole hydrochloride.

Example 2

(RS) 8-Chloro-1,2,3,4,10,10a-hexahydropyrazino[1,2-a]indole hydrochloride

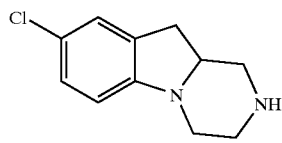

Ethyl 5-chloro-1-(cyanomethyl)indole-2-carboxylate

The compound was prepared according to the procedure described by Rajur, Sharanabasava B. et al. (*Indian J. Chem., Sect. B*, (1989), 28B(12), 1065–8).

8-Chloro-1,2,3,4-tetrahydropyrazino[1,2-a]indole hydrochloride

The compound was prepared according to the procedure described by Rajur, Sharanabasava B. et al. (*Indian J. Chem, Sect. B* (1989), 28B(12), 1065–8) with modifications as described below:

To a stirred suspension of lithium aluminium hydride (95%; 915 mg, 22.91 mmol) in anhydrous ether (40 mL) under Ar at ambient temperature was added a slurry of ethyl 5-chloro-1-(cyanomethyl)indole-2-carboxylate (3.0 g, 11.4 mmol) in anhydrous ether (110 mL, then 90 mL rinse), over 30 min while keeping the internal temperature below 30° C. The resultant mixture was heated at reflux for 5 h, then allowed to cool to ambient temperature. Water (0.91 mL) was cautiously added, followed by 15% aqueous sodium hydroxide solution (0.91 mL), water (2.75 mL), and magnesium sulfate. The reaction mixture was filtered, the filter-cake washed with chloroform-methanol (9:1) and the filtrate was concentrated in vacuo to afford the crude product as a grey-green oil. Purification by flash column chromatography [$SiO_2$; ethyl acetate-methanol-ammonium hydroxide (9:1:0→92:7:1→90:10:5)] afforded a colourless oil (1.057 g, 45%). To a solution of the above oil (433 mg, 2.1 mmol) in acetone (1.5 mL) was added ethereal HCl (1 M; 6.3 mL, 6.3 mmol) followed by ether (1.5 mL). The resultant suspension was filtered and washed with ether to afford the title compound (486 mg, 95%) as a white solid: mp 275° C. (dec); Found C, 54.17; H, 5.01; N, 11.39%. $C_{11}H_{11}ClN_2 \cdot HCl$ requires: C, 54.34; H, 4.97; N, 11.52%.

(RS) 8-Chloro-1,2,3,4,10,10a-hexahydropyrazino[1,2-a]indole hydrochloride

To a stirred solution of 8-chloro-1,2,3,4-tetrahydropyrazino[1,2-a]indole (600 mg, 2.90 mmol) in acetic acid (20 mL) under Ar at 10° C. was added sodium cyanoborohydride (608 mg, 9.68 mmol) and the resultant mixture was allowed to warm to ambient temperature. After 16 h, water (100 mL) was added followed by cautious addition of ammonium hydroxide solution (to pH 8). The mixture was extracted with chloroform (3×50 mL) and the combined extracts were washed with brine (50 mL), dried (magnesium sulfate) and evaporated to afford the crude product as a yellow oil. Purification by flash column chromatography [$SiO_2$, ethyl acetate-methanol-ammonium hydroxide (92:7:1)] afforded a pale yellow oil (420 mg, 69%). To a solution of the above oil (371 mg, 1.78 mmol) in acetone (3 mL) was added ethereal HCl (1 M; 5.3 mL, 5.3 mmol) followed by ether (3 mL). The resultant solid was collected by filtration and washed with ether to afford the title compound (393 mg, 90%) as a white solid: mp 258–262° C. (dec); Found C, 53.80; H, 5.77; N, 11.33%. $C_{11}H_{13}ClN_2 \cdot HCl$ requires: C, 53.89; H, 5.76; N, 11.42%.

Example 3

(RS) 9-Chloro-1,2,3,4,10,10a-hexahydropyrazino[1,2-a]indole hydrochloride

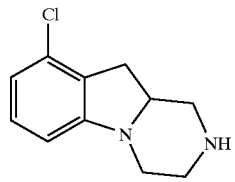

Ethyl 4-chloroindole-2-carboxylate

Potassium tert-butoxide (11.22 g, 0.1 mol) was added portionwise to stirred ethanol (25 mL) under Ar at ambient temperature. When the resultant viscous solution had cooled sufficiently, ether (300 mL) was added followed by diethyl oxalate (13.6 mL, 0.1 mol). After 10 min, 2-chloro-6-nitrotoluene (17.16 g, 0.1 mol) was added and the yellow solution became dark red. The reaction mixture was transferred to a conical flask and was stoppered and left standing at ambient temperature for 4 h, and was then transferred to the fridge for 65 h. The solid was collected by filtration, washed with ether until the filtrate ran colourless, and was sucked dry for 15 min. The isolated product (22.61 g, 73%) was used without further purification.

To a solution of the above solid (11.2 g, 36.2 mmol) in acetic acid (250 mL) was added iron powder (7.08 g, 127 mmol) and the mixture was heated to 90° C. (external). As the external temperature reached ~90° C. an exotherm became apparent, with the internal temperature reaching 100° C. The mixture became a light brown suspension, and after 15 min the exotherm had subsided. After a further 3 h at 90° C. the reaction was allowed to cool to 45° C. and was then poured into ice-water (500 mL). The mixture was extracted with ether (3×400 mL) and the combined extracts were washed with saturated aqueous sodium bicarbonate solution (repeated until effervescence ceased), water (400 mL), and 1N HCl (2×300 mL). The organic extracts were dried (magnesium sulfate) and the solvent removed in vacuo to afford the crude product as a yellow-orange oil (5.38 g). This material was dissolved in dichloromethane and passed down a short plug of silica. Removal of solvent afforded the title compound (4.38 g, 54%) as a pale-yellow solid: IR $v_{max}$ (Nujol)/$cm^{-1}$ 3314, 2988, 2957, 2925, 2855, 1690, 1618, 1568, 1525, 1439, 1382, 1339, 1290, 1255, 1210, 1188, 1144, 1127, 1024, 977, 946, 822, 765, 674, 642, 598, 522 and 517; NMR $\delta_H$ (400 MHz, $CDCl_3$) 1.43 (3H, t, J 7 Hz), 4.44 (2H, q, J 7 Hz), 7.16 (1H, dd, J 7.5, 1 Hz), 7.23 (1H, t, J 7.5 Hz), 7.32 (1H, dd, J 4.5, 1 Hz), 7.33 (1H, d, J 7 Hz).

Ethyl 4-chloro-1-(cycmomethyl)indole-2-carboxylate

To a stirred solution of ethyl 4-chloroindole (6.57 g, 29.4 mmol) in DMF (60 mL) under Ar at ambient temperature was added sodium hydride (60%; 1.76 g, 44 mmol) portionwise over 10 min. After 30 min, a solution of chloroacetonitrile (3.7 ml, 58.5 mmol) in DMF (10 mL) was added and the mixture was heated to an external temperature of 75° C. After 45 min, the reaction was allowed to cool to ambient temperature and was poured onto ice (300 mL). When the ice had melted, the resultant suspension was filtered and the crude solid was washed with water and sucked dry. Recrystallisaton (Ethanol, 100 mL, reflux) afforded the title compound (6.17 g, 80%) as an off-white crystalline solid: mp 143–144° C.; Found C, 59.47; H, 4.19; N, 10.65%. $C_{13}H_{11}ClN_2O_2$ requires: C, 59.44; H, 4.22; N, 10.66%.

9-Chloro-12,3,4-tetrahydropyrazino[1,2-a]indole hydrochloride

To a stirred suspension of lithium aluminium hydride (95%; 1.52 g, 38.1 mmol) in anhydrous ether (200 mL) under Ar at ambient temperature was added ethyl 4-chloro-1-(cyanomethyl)indole-2-carboxylate (4.0 g, 152 mmol) portionwise over 30 min, keeping the internal temperature below 25° C. The resultant mixture was heated at reflux for 16 h, then allowed to cool to ambient temperature. Water (1.5 mL) was cautiously added, followed by 15% aqueous sodium hydroxide solution (1.5 mL), water (4.5 mL), and magnesium sulfite. The reaction mixture was filtered through celite, the filter-cake washed with ether and the solvent removed in vacuo to afford the crude product. Purification by flash column chromatography [SiO$_2$; ethyl acetate-methanol-ammonium hydroxide (9:1:0→90:8:2)] afforded a pale yellow solid (1.377 g, 440%). To a solution of the above solid (150 mg, 0.73 mmol) in acetone (0.5 mL) was added ethereal HCl (1 M; 1.5 mL, 1.5 mmol) followed by ether (0.5 mL). The resultant suspension was filtered and washed with ether to afford the title compound (162 mg, 92%) as a pale yellow solid: mp 275° C. (dec); Found C, 54.37; H, 5.04; N, 11.40%. C$_{11}$H$_{11}$ClN$_2$.HCl requires: C, 54.34; H, 4.97; N, 11.520%.

(RS) 9-Chloro-1,2,3,4,10,10a-hexahydropyrazino[1,2-a]indole hydrochloride

To a stirred solution of 9-chloro-1,2,3,4-tetrahydropyrazino[1,2-a]indole (1.186 g, 5.74 mmol) in acetic acid (40 mL) under Ar at 10° C. was added sodium cyanoborohydride (1.19 g, 18.9 mmol) and the reaction mixture was allowed to warm to ambient temperature. After 16 h, the mixture was poured into water (200 mL) and ammonium hydroxide was added (to pH 8). The resultant mixture was extracted with chloroform (3×75 mL) and the combined extracts were washed with brine (75 mL), dried (magnesium sulfite) and concentrated under vacuum to afford the crude product as a pale yellow oil. Purification by flash column chromatography [SiO$_2$; ethyl acetate-methanol-ammonium hydroxide (92:7:1)] afforded a colourless oil (650 mg, 54%). To a solution of the above oil (650 mg, 3.11 mmol) in acetone (3 mL) was added ethereal HCl (1 M; 9.3 mL, 9.3 mmol) followed by ether (3 mL). The resultant suspension was filtered and washed with ether to afford the title compound (738 mg, 97%) as a white solid: mp 265–269° C. (dec); Found C, 53.64; H, 5.73; N, 11.42%. C$_{11}$H$_{13}$ClN$_2$.HCl requires: C, 53.89; H, 5.76; N, 11.42%.

Example 4

(RS) 7-Bromo-1,2,3,4,10,10a-hexahydropyrazino[1,2-a]indole hydrochloride

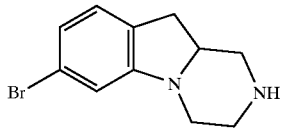

Ethyl 4-bromo-2-nitrophenyl acetate, potassium salt

Potassium tert-butoxide (11.2 g, 100 mmol) was added in 1 portion to stirred ethanol (25 mL) at room temperature (heat evolved). The solution was then diluted with ether (300 mL) and diethyl oxalate (13.6 mL, 100 mmol) was added in 1 portion. The reaction was stirred at room temperature for 10 min then 4-bromo-2-nitrotoluene (21.6 g, 100 mmol) was added in 1 portion. The reaction was then heated to reflux and stirred for 3 hours. Afer allowing to cool to room temperature the mixture was cooled to 4° C., left for 18 h and filtered The filter-cake was washed with ether (2×150 mL) and dried to give the product as a red solid (21.4 g, 68%). IR $v_{max}$ (Nujol)/cm$^{-1}$ 3408, 2925, 2855, 1732, 1675, 1649, 1594, 1560, 1512, 1465, 1378, 1366, 1347, 1240, 1208, 1148, 1110, 1088, 931, 899, 878, 831, 804, 775, 761 and 683; NMR $\delta_H$ (400 MHz; DMSO-d$_6$) 9.36 (1H, d, J 9 Hz), 7.90 (1H, d, J 2.4 Hz), 7.32 (1H, dd, J 9 Hz, 2.4 Hz), 6.56 (1H, s), 4.06 2H, q, J 7 Hz), 3.36 (1H br. s, OH), 1.22 (3H, t,J 7 Hz).

Ethyl 6-bromoindole-2-carboxylate

Iron powder (5.34 g, 95 mmol) was added in 1 portion to a stirred solution of ethyl 4-bromo-2-nitrophenyl acetate, potassium salt (10 g, 32 mmol) in acetic acid (100 mL) at room temperature under Ar. The reaction was heated to 90° C. and stirred for 45 min. After allowing to cool to room temperature the mixture was poured into saturated sodium hydrogen carbonate solution (~200 mL) and filtered through celite washing with ethyl acetate (300 mL). The filtrate was extracted with ethyl acetate (2×200 mL) and the combined organic extracts were dried (sodium sulfate), filtered and concentrated in vacuo to leave a crude solid. The solid was purified by flash column chromatography [SiO$_2$; Ethyl acetate-heptane (5:1)→Ethyl acetate)] to give the product as a yellow solid (4.6 g, 54%). IR $v_{max}$ (Nujol)/cm$^{-1}$ 3318, 2925, 2855, 1880, 1694, 1618, 1569, 1523, 1486, 1462, 1423, 1375, 1349, 1317, 1239, 1221, 1205, 1120, 1105, 1047, 1023, 975, 942, 911, 868, 852, 822, 792, 766, 735, 658, 590, 583 and 548; NMR $\delta_H$ (400 MHz; CDCl$_3$) 9.0 (1H, br. s), 7.59 (1H, s), 7.53 (1H, d, J 8.5 Hz), 7.24 (1H, dd, J 8.5, 1.6 Hz), 7.18 (1H, d, J 1.6 Hz), 4.39 (2H, q, J 7 Hz), 1.40 (3H, t, J 7 Hz).

Ethyl 6-bromo-1-(cyanomethyl)indole-2-carboxylate

A solution of ethyl 6-bromoindole-2-carboxylate (4.4 g, 16.4 mmol) in DMF (20 mL) was added dropwise over ~2–3 min to a stirred suspension of sodium hydride (60%, 1.0 g, 25 mmol) in DMF (20 mL) at 0° C. under Ar. The reaction was stirred at 0° C. for 45 min then chloroacetonitrile (2.1 mL, 33 mmol) was added in one portion. The reaction was then heated to 75° C. and stirred for 1 h. After allowing to cool to room temperature the mixture was poured into water (150 mL) and extracted with ethyl acetate (3×75 mL). The combined organic extracts were washed with brine (75 mL), dried (magnesium sulfate), filtered and the solvent removed under vacuum to leave a crude solid which was purified by flash column chromatography (SiO$_2$; ethyl acetate) to give the product as a yellow solid (4.8 g, 95%). IR $v_{max}$ (Nujol)/cm$^{-1}$ 3320, 3089, 2925, 2855, 1898, 1705, 1609, 1530, 1521, 1470, 1449, 1427, 1400, 1394, 1377, 1367, 1336, 1308, 1265, 1205, 1151, 1134,1108, 1054, 1027, 993, 950, 90, 873, 841, 832, 802, 792, 762, 736, 663, 615 and 589; NMR OH (400 MHz; CDCl$_3$) 7.61 (1H, s), 7.57 (1H, d, J.8.5 Hz), 7.37 (1H, d, J 1.5 Hz), 7.35 (1H, dd, J 8.5 Hz, 1.5 Hz), 5.57 (2H, s), 4.45 (2H, q, J 7.2 Hz), 1.42 (3H, t, J 7.2 Hz).

7-Bromo 1,2,3,4-tetrahydropyrazino[1,2-a]indole

Ethyl 6-bromo-1-cyanomethylindole-2-carboxylate (3.1 g, 10 mmol) was added portionwise over 2–3 min to a stirred suspension of lithium aluminium hydride (0.95 g, mmol) in ether (100 mL) at room temperature under Ar. The reaction was then heated to reflux and stirred for 18 h. After allowing to cool to room temperature the mixture was poured slowly into stirred saturated aqueous sodium potassium tartrate solution (300 mL). The mixture was stirred for 10 min and ethyl acetate (200 mL) was added. The mixture was then filtered through celite and extracted with ethyl acetate (2×150 mL). The combined organic extracts were washed with brine (150 mL), dried (magnesium sulfate), filtered and the solvent removed under vacuum to leave a crude oil. The oil was purified by flash column chromatography [SiO$_2$; methanol-ethyl acetate-ammonium hydroxide (1:9:0)→(9:90:1)] to give the product as a yellow oil (1.1 g, 44%). IR $v_{max}$ (Nujol)/cm$^{-1}$ 3310, 2925, 2855, 2725, 1886, 1666, 1604, 1563, 1535, 1458, 1411, 1378, 1366, 1340, 1321, 1301, 1278, 1242, 1217, 1201, 1169, 1139, 1128, 1114, 1048, 1000, 945, 924, 876, 844, 835, 812, 792, 751, 730, 699, 648, 619, 590, 562, 523 and 490. NMR $\delta_H$ (400 MHz; CDCl$_3$) 7.42 (1H, m), 7.39 (1H, d, J 8.7 Hz), 7.19 (1H, dd, J 8.7 Hz, 2Hz), 6.17 (1H, m), 4.20 (2H, d, J 0.8 Hz), 3.97 (2H, t, J 5.8 Hz), 3.35 (2H, t, J 5.8 Hz), 1.63 (1H, br. s).

(RS) 7-Bromo-1,2,3,4,10,10a-hexahydropyrazino[1,2-a]indole hydrochloride

Sodium cyanoborohydride (95%, 0.85 g, 13 mmol) was added portionwse over 2 min to a stirred solution of 8-bromo-1,2,3,4-tetrahydropyrazino[1,2-a]indole (1.0 g, 4 mmol) in acetic acid (25 mL) at 10° C. under Ar. The reaction was stirred at 0° C. for 20 min then allowed to warm to room temperature and stirred for 18 h. The mixture was then cautiously poured into saturated aqueous sodium bicarbonate solution (~250 mL) and ethyl acetate (100 mL). The aqueous and organic layers were partitioned and the aqueous was extracted with ethyl acetate (3×100 mL). The combined organic extracts were washed with brine (1×100 mL), dried (magnesium sulfate), filtered and the solvent removed under vacuum to leave a crude oil. The oil was purified by flash column chromatography [SiO$_2$; ethyl acetate-methanol-ammonium hydroxide (90:8:2)] to give a colourless oil (0.82 g, 79%). The oil (0.82 g) was dissolved in ether (10 mL) and ethereal hydrogen chloride solution (1.0 M, 7 mL) was added. The solvent was removed under vacuum and the solid was triturated with ether to give the product as a white solid (0.72 g, 61%). mp 243–245° C. Found. C, 45.44; H, 4.93; N, 9.57%. C$_{11}$H$_{13}$BrN$_2$.HCl requires: C, 45.62; H, 4.87; N, 9.67%. IR $v_{max}$ (Nujol)/cm$^{-1}$ 3180, 3112, 3044, 2925, 2854, 2700, 2605, 2499, 2452, 1720, 1607, 1591, 1486, 1458, 1401, 1389, 1377, 1360, 1341, 1323, 1306, 1290, 1269, 1222, 1198, 1174, 1126, 1100, 1072, 1059, 1020, 987, 938, 930, 915, 888, 866, 839, 804, 776, 750, 722, 645 and 592. NMR $\delta_H$ (400, DMSO-d$_6$) 9.52 (2H, br. s), 7.04 (1H, d, J 7.5 Hz), 6.84 (1H, d, J 1.7 Hz), 6.79 (1H, d, J 7.5 Hz), 3.83–3.91 (2H, m), 3.81–3.34 (3H, m), 2.81–3.05 (3H, m), 2.56–2.62 (1H, m).

Example 5

(RS) 7-Chloro-8-methyl-1,23,4,10,10a-hexahydropyrazino[1,2-a]indole fumarate

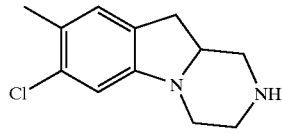

5-Nitro-2,4-xylidine

Conc. nitric acid (33 g) was added dropwise over 3 h to a stirred solution of m-xylidine (40 g, 0.33 mmol) in conc. sulfuric acid (400 g) at <15° C. After complete addition the reaction was stirred at 15° C. for 1 h then poured onto ice (600 mL), stirred for 30 min and filtered The yellow filter-cake was neutralised with saturated aqueous sodium hydrogen carbonate solution (500 mL) and extracted with ethyl acetate (3×200 mL). The combined organic extracts were dried (Magnesium sulfate), filtered and the solvent removed under vacuum to leave a crude solid. The solid was recrystalised (ethanol-water) to give the product as an orange solid (39 g, 71%, contains 20% di-nitro). IR $v_{max}$ (Nujol)/cm$^{-1}$ 3469, 3386, 3239, 2956, 2925, 2855, 1719, 1636, 1514, 1461, 1377, 1339, 1297, 1273, 1222, 1170, 1034, 992, 885, 870, 849, 805, 758, 745, 723, 640, 607 and 571; NMR $\delta_H$ (400 MHz; CDCl$_3$) 7.15 (1H, s), 6.87 (1H, s), 4.99 (2H, br. s), 2.21 (3H, s), 1.97(3H, s).

4-Chloro-6-nitro-m-xylene

A solution of sodium nitrite (7.2 g, 0.1 mol) in water (20 mL) was added dropwise over 45 min at <5° C. to a stirred suspension of 5-nitro-2,4-xylidine (16.6 g, 0.1 mol) in conc. hydrochloric acid (300 mL). After complete addition the reaction was stilted at <5° C. for 1 h then a solution of copper(I)chloride (16.0 g, 0.16 mol) in conc. hydrochloric acid (50 mL) was added dropwise over 20 min at <5° C. (CARE: effervescence at first). The reaction was then warmed from 0° C. to room temperature and stirred for 18 h. The mixture was then carefully poured into water (1 L) and extracted with ethyl acetate (3×300 mL). The combined organic extracts were dried (magnesium sulfate), filtered and the solvent removed under vacuum to leave a crude oil. The oil was purified by flash column chromatography (SiO$_2$; heptane) to give the product as a yellow oil (8.8 g, 47%). IR $v_{max}$ (film)/cm$^{-1}$ 3103, 2985, 2935, 2863, 2744, 2432, 1610, 1572, 1518, 1480, 1454, 1384, 1346, 1286, 1266, 1244, 1197, 1166, 1157, 1107, 1036, 982, 894, 842, 759, 746, 725, 704, 646 and 602; NMR $\delta_H$ (400 MHz; CDCl$_3$) 8.01 (1H, s), 7.20 (1H, s), 2.56 (3H, s), 2.41 (3H, s).

Ethyl 4-chloro-3-methyl-2-nitrophenylacetate, potassium salt

Potassium tert-butoxide (5.3 g, 47 mmol) was added in 1 portion to stirred ethanol (10 mL) at 0° C. under Ar. The mixture was diluted with ether (140 mL) and then diethyl oxalate (6.5 mL, 47 mmol) was added in 1 portion. After 2 min 4-chloro-6-nitro-m-xylene (8.8 g, 47 mmol) was added in 1 portion. The reaction was stirred at room temperature for 40 h. The mixture was filtered and the filter cake was washed with ether and dried to give the crude product as a red solid (6.5 g) which was used immediately.

Ethyl 6-chloro-5-methylindole-2-carboxylate

Iron powder (3.34 g, 60 mmol) was added in 1 portion to a stirred solution of ethyl 4-chloro-3-methyl-2-nitrophenylacetate, potassium salt (6.5 g, 20 mmol) in acetic acid (60 mL) at room temperature under Ar. The reaction was then heated to 90° C. and stirred for 1 h. After allowing to cool to room temperature the mixture was cautiously poured into saturated aqueous sodium hydrogen carbonate solution (200 mL) containing solid sodium hydrogen carbonate (10 g) and ethyl acetate (200 mL). The mixture was filtered through celite and the aqueous and organic layers were separated. The aqueous layer was extracted with ethyl acetate (2×200 mL) and the combined organic extracts were washed with brine (1×200 mL), dried (magnesium sulfate), filtered and the solvent removed under vacuum to leave a crude solid. The solid was adsorbed onto sodium sulfate (10 g) and purified by flash column chromatography [SiO$_2$; ethyl acetate-heptane (1:5)→(1:0)] to give the product as yellow solid (1.6 g, 14% over 2 steps). IR $v_{max}$ (Nujol)/cm$^{-1}$ 3319,2925, 2855, 1683, 1623, 1570, 1530, 1555, 1418, 1368, 1339, 1330, 1280, 1241, 1158, 1120, 1107, 1021, 996, 976, 885, 855, 828, 773,736,664, 580, 574, 514 and 489; NMR $\delta_H$ (400 MHz; CDCl$_3$) 8.82 (1H, br. s), 7.52 (1H, s), 7.44 (1H, s), 7.12 (1H, m), 4.39 (2H, q, J 7.1 Hz), 2.45 (3H, s), 1.40 (3H t, J 7.1 Hz).

Ethyl 6-chloro-1-(cyanomethyl)-5-methylindole-2-carboxylate

A solution of ethyl 6-chloro-5-methylindole-2-carboxylate (1.5 g, 6.3 mmol) in DMF (30 mL) was added dropwise to a stirred suspension of sodium hydride (60%, 0.39 g, 10 mmol) in DMF (20 mL) at room temperature under Ar. The reaction was then cooled to 0° C. and stirred for 45 min then chloroacetonitrile (0.81 mL, 13 mmol) was added in one portion. The reaction was heated to 75° C. and stirred for 1 h. After allowing to cool to room temperature the mixture was poured into water (200 mL) and with ethyl acetate (3×100 mL). The combined organic extracts were washed with brine (1×100 mL), dried (magnesium sulfate), filtered and the solvent removed under vacuum to leave the crude product which was used immediately.

7-Chloro-8-methyl-1,2,3,4-tetrahydropyrazino[1,2-a]indole

Ethyl 6chloro-1-(cyanomethyl)-5-methylindole-2-carboxylate (1.75 g, 6.3 mmol) was added portionwise over 2 min to a stirred solution of lithium aluminium hydride (0.61 g, 16 mmol) in ether (50 mL) at room temperature under Ar. The reaction was then heated to reflux and stirred for 70 h. The mixture was cooled to room temperature, a further portion of lithium aluminium hydride (0.61 g) was added and the reaction was heated to reflux and stirred for 18 h. The mixture was allowed to cool and then poured into aqueous potassium sodium tare solution (200 mL) and ethyl acetate (150 mL). The mixture was filtered through celite and the aqueous and organic layers were separated. The aqueous was extracted with ethyl acetate (2×100 mL) and the combined organic extracts were washed with brine (1×100 mL) dried (magnesium sulfate), filtered and the solvent removed under vacuum to leave a crude oil. The oil was purified by flash column chromatography [SiO$_2$; ethyl acetate-methanol, (100:0)→(9:1)] to give the product as a yellow solid (027 g, 19%). IR $v_{max}$ (Nujol)/cm$^{-1}$ 3351, 3190, 2922, 2731, 1734, 1647, 1615, 1562, 1543, 1457, 1416, 1378, 1350, 1316, 1304, 1261, 1246, 1223, 1182, 1157, 1134, 1116, 1028, 983, 972, 962, 902, 883, 835, 800, 782, 732, 700, 666, 632, 617, 558, 510 and 496; NMR $\delta_H$ (400 MHz; CDCl$_3$) 7.35 (1H, s), 725 (1H, s), 6.06 (1H, m), 4.16 (2H, s), 3.91 (2H, t, J 5.5 Hz), 3.31 (2H, t, J 5.5 Hz), 2.42 (3H, s).

(RS) 7-Chloro-8-methyl-1,2,3,4,10,10a-hexahydropyrazino[1,2-a]indole

Sodium cyanoborohydride (95%, 0.24 g, 3.6 mmol) was added in 1 portion to a stirred solution of 7-chloro-8-methyl-1,2,3,4-tetrahydropyrazino[1,2-a]indole (0.25 g, 1.1 mmol) in acetic acid (10 mL) at 10° C. under Ar. The reaction was then allowed to warm to room temperature and stirred for 4 h. The mixture was then poured into saturated aqueous sodium hydrogen carbonate solution (100 mL) and extracted with ethyl acetate (3×50 mL). The combined organic extracts were washed with brine (1×50 mL), dried (magnesium sulfate), filtered and the solvent removed under vacuum to leave a crude oil. The oil was purified by flash column chromatography [SiO$_2$; ethyl acetate-methanol-ammonium hydroxide (9:1:0)→(90:9:1)] to give an oil (022 g, 87%). The oil was dissolved in boiling 2-propanol (5 mL) and a solution of fumaric acid (0.05 g) in hot 2-propanol (5 mL) was added. The solvent was removed under vacuum and the residue triturated with ether to give the product as an off-white solid (40 mg, 10%). mp 180–182° C. IR $v_{max}$ (Nujol)/cm$^{-1}$ 4331, 2924, 2854, 1702, 1618, 1459, 1377, 1274, 1176, 1103, 1008, 969, 868, 834, 786, 722, 676, 642 and 537; NMR $\delta_H$ (400 MHz; DMSO-d$_6$) 7.02 (1H, s), 6.60 (1H, s), 6.54 (3H, s), 3.63–3.67 (1H, m), 3.47–3.57 (2H, m), 2.88–3.10 (5H, m), 2.72–2.79 (1H, m), 2.19 (3H, s).

Example 6

(RS) 7-Chloro-1,2,3,4,10,10a-6-aza-hexahydropyrazino[1,2-a]-7-indole fumarate

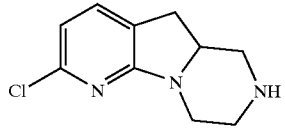

(RS) Ethyl 2-hydroxy-1-tert-butoxycarbonyl-7-azaindoline-2-carboxylate

To a stirred solution of 2-tert-butoxycarbonylamino-3-methylpyridine (1.0 g, 4.8 mmol) in THF (10 mL) at −10° C. under Ar was added dropwise a solution of n-butyllithium (1.6 M, 6.0 mL, 9.6 mmol). The mixture was stirred for 30 min then added dropwise via cannula to a stirred solution of diethyl oxalate (2.1 g, 14.4 mmol) in THF (10 mL) at 0° C. under Ar. The mixture was stirred for 1 h and partitioned between water (50 mL) and ethyl acetate (30 mL). The aqueous layer was extracted with ethyl acetate (20 mL). The combined organic extracts were washed (water, brine), dried (sodium sulfate), concentrated in vacuo and purified by column chromatography [SiO$_2$; ethyl acetate-heptane (1:1)] to give the product as a clear oil (0.61 g, 47%). IR $v_{max}$ (film)/cm$^{-1}$ 3475, 2982, 2935, 2237, 1740, 1695, 1606, 1592, 1433, 1371, 1310, 1248, 1209, 1188, 1159, 1099, 1065, 1023, 912, 855, 785, 770, 732 and 645; NMR $\delta_H$ (400 MHz, CDCl$_3$) 1.27 (3H, t, J 7Hz), 1.53 (9H, s), 3.18 (1H, d, J 17 Hz), 3.40 (1H, d, J 17 Hz), 4.27 (2H, q, J 7 Hz), 6.90 (1H, dd, J, 2.5,5 Hz), 7.43 (1H, d, J 7 Hz), 8.26 (1H, d, J 3.5 Hz).

Ethyl 7-azaindole-2-carboxylate

To a stirred solution of (RS) ethyl (2-hydroxy-1-tert-butoxycarbonyl-7-azaidoline-2-carboxylate) (0.6 g, 1.9 mmol) in ethanol (20 mL) was added dropwise concentrated hydrochloric acid (0.6 mL). The mixture was heated under reflux for 2 h, cooled to room temperature and partitioned between ether (30 mL) and aqueous sodium hydrogen carbonate solution (30 mL). The organic layer was washed (water, brine), dried (sodium sulfate) and concentrated in vacuo to give ethyl 7-azaindole-2-carboxylate as a white solid (0.26 g, 70%). mp 153–6° C. Found: C, 62.84; H, 5.34; N, 14.50%. C$_{10}$H$_{10}$N$_2$O$_2$ requires: C, 63.15; H, 5.30; N, 14.72%.

Ethyl 7-azaindole-2-carboxylate-7-oxide

To a stirred solution of ethyl 7-azaindole-2carboxylate (4.8 g, 25 mmol) in ether (200 mL) at 0° C. was added portionwise 3-chloroperbenzoic acid (~57%, 8.0 g, ~26 mmol). The mixture was warmed to room temperature, stirred for 4 h, concentrated in vacuo and partitioned between aqueous sodium hydrogen carbonate solution (100 mL) and chloroform (100 mL). The aqueous layer was extracted with chloroform (50 mL). The combined chloroform extracts were washed (brine), dried (sodium sulfate) and concentrated in vacuo to give a gum (1.8 g) which was crystallised from isopropyl ether/ethanol to give ethyl 7-azaindole-2-carboxylate-7-oxide as a white crysalline solid (1.4 g, 27%). mp 159–60° C. Found: C, 58.40; H, 4.95; N, 13.53%. C$_{10}$H$_{10}$N$_2$O$_3$ requires: C, 58.25; H, 4.89; N, 13.58%.

Ethyl 6-chloro-7-azaindole-2-carboxylate

To a stirred solution of ethyl 7-azaindole-2-carboxylate-7-oxide (1.32 g, 6.4 mmol) and hexamethyldisilazane (1.4 mL, 6.6 mmol) in THF (30 mL) at 0° C. was added dropwise over 30 min a solution of methyl chloroformate (12 mL, 15.5 mmol) in THF (5 mL). The mixture was warmed to room temperature, stirred for 2 h and partitioned between ether (50 mL) and water (50 mL). The aqueous layer was extracted with ether (30 mL). The combined organic extracts were washed (water, brine), dried (sodium sulfate) and purified by column chromatography [SiO$_2$; heptane—ether (3:1)1 to give ethyl 6-chloro-7-azaindole-2-carboxylate as a white solid (0.38 g, 26%). mp 144–145° C. Found: C, 53.69; H, 4.05; N, 12.39%. C$_{10}$H$_9$N$_2$ClO$_2$ requires: C, 53.47; H, 4.04; N, 12.46%.

Ethyl 6-chloro-1-(cyanomethyl)-7-azaindole-2-carboxylate

To a stirred suspension of sodium hydride (60%, 0.11 g, 2.8 mmol) in DMF (20 mL) was added a solution of ethyl 6-chloro7-azaindole-2-carboxylate (0.52 g, 23 mmol) in DMF (1 mL). The mixture was stirred for 1 h then treated with chloroacetonitile (0.18 mL, 2.8 mmol); The mixture was heated to 60° C.; stirred for 3 h, cooled to room temperature, poured into ice-water (50 mL) and filtered. The filter-cake was washed (water, heptane) and dried to give ethyl 6-chloro-7-azaindole-1-cyanomethyl-2-carboxylate as a white solid (0.58 g, 94%). A sample recrystallised from isopropyl ether/2-propanol gave mp 148° C. Found: C, 54.69; H, 3.82; N, 15.85%. C$_{12}$H$_{10}$N$_3$ClO$_2$ requires: C, 54.66; H, 3.82; N, 15.93%.

7-Chloro-1,2,3,4-tetrahydro-6-aza-pyrazino[1,2-a]indole

To a stirred suspension of lithium aluminium hydride (0.16 g, 4.2 mmol) in ether (20 mL) at 0° C. under Ar was added ethyl 6-chloro1-(cyanomethyl)-7-azaindole-2-carboxylate (0.45 g, 1.7 mmol). The mixture was heated under reflux for 18 h, cooled to room temperature and treated with sodium sulfate decahydrate (2.8 g, 8.4 mmol). The mixture was stirred for 30 min, filtered through kieselguhr, concentrated in vacuo and purified by column chromatography [SiO$_2$; ethyl acetate-methanol (9:1)] to give the product as a yellow oil (0.10 g, 27%). IR $\nu_{max}$ (Nujol)/cm$^{-1}$ 3230, 2925, 2855, 1594, 1561, 1528, 1466, 1429, 1397, 1342, 1306, 1257, 1121, 1100, 1022, 948, 901, 874, 822, 810, 746, 546 and 509; NMR $\delta_H$ (400 MHz, CDCl$_3$), 3.31 (2H, t, J 6 Hz), 4.15 (2H, t, J 6 Hz), 4.19(2H, s), 6.11 (1H, s), 7.03 (1H, d, J 8 Hz), 7.72 (1H, d, J 8 Hz).

(RS) 7-Chloro-1,2,3,4,10,10a-hexahydro-6-aza-pyrazino[1,2a-indole fumarate

To a stir solution of 7-chloro-1,2,3,4-tetrahydro-6-aza-pyrazino[1,2-a]-indole (0.06 g, 0.3 mmol) in acetic acid (2 mL) was added sodium cyanoborohydride (95%, 0.1 g, 1.5 mmol). The mixture was stirred for 18 h and partitioned between aqueous sodium hydrogen carbonate solution (20 mL) and dichloromethane (30 mL). The aqueous layer was extracted with dichloromethane (10 mL). The combined organic extracts were washed (water, brine), dried (sodium sulfate), concentrated in vacuo and purified by column chromatography [SiO$_2$; ethyl acetate-methanol-ammonium hydroxide (79:20:1)] to give an oil (0.009 g). The oil was dissolved in 2-propanol (0.2 mL) and added to a solution of fumaric acid (0.006 g, 0.05 mmol) in 2-propanol (0.1 mL) at 50° C. The solution was cooled to 0° C. and filtered The filter-cake was washed with ether and dried to give the product as an off-white solid (0.005 g, 5%). NMR $\delta_H$ (400 MHz, DMSO-d$_6$) 2.5 (3H, m), 2.9 (4H, m), 3.8 (2H, m), 6.45 (1H, d, J 7.5 Hz), 6.55 (2H, s, 726 (1H, d, J 7.5 Hz); m/z (S$^+$) Found: 210 (MH$^+$) and 212 (MH$^+$). C$_{10}$H$_{12}$ClN$_3$ requires: 210(MH$^+$) and (MH$^+$).

Example 7

(10aS) 7-Chloro-1,2,3,4,10,10a-hexahydropyrazino[1,2-a]indole hydrochloride

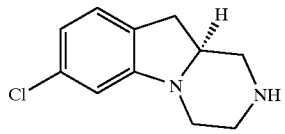

(RS) 7-Chloro-2-(trifluoroacetyl)-1,3,4,10,10a-pentahydropyrazino[1,2-a]indole

To a stirred solution of 7-chloro-1,2,3,4,10,10a-hexahydropyrazino[1,2-a]indole (70 mg, 0.34 mmol) in dichloromethane (3 mL) at 0° C. was added trifluoroacetic anhydride (0.05 mL, 035 mmol). After 30 min the reaction mixture was passed through a small, ether-wet pad of silica, and was washed through with ether. Removal of solvent in vacuo afforded the title compound (100 mg, 96%) as a pale yellow oil: NMR $\delta_H$ (400 MHz, CDCl$_3$), 2.61 (1H, dq, J 14, 7.5 Hz), 2.84 (0.5H, t, J 12 Hz), 2.98 (0.5H, ddd, J 14, 12, 2.5 Hz), 3.03 (2H, m), 3.28 (0.5H, dd, J 13.5, 11.5 Hz), 3.54 (0.5H, ddd, J 14, 12, 3 Hz), 3.59 (2H, m), 3.96 (1H, m), 4.56 (1H, m), 6.45 (1H, dd, J 11, 1.5 Hz), 6.68 (1H, dt, J 7.5, 1.5 Hz) and 7.00 (1H, q, J 4 Hz); hplc [Supelcosil ABZ$^+$Plus (170 mm×4.6 mm), 5 μm, methanol-10 mM aqueous ammonium acetate solution (80:20) mobile phase, 1 mL/min 230 nm detection] 90% at 3.55 min.; chiral hplc [30 μL injection volume, ChiralCel OD column (300 mm×4.6 mm), hexane-isopropanol (90:10) mobile phase, 1 mL/min 30 min run, 220 nm detection]. 49.9% at 13.2 min, 50.1% at 18.7 min (10aS) 7-Chloro 2-(trifluoroacetyl)-1,3,4,10,10a-pentahydropyrazino[1,2-a]indole (RS) 7-Chloro-2-(trifluoroacetyl)-1,3,4,10,10a-pentahydropyrazino[1,2a]indole was separated into the constituent enantiomers by repeat injection of a solution in dichloromethane (~0.1 mg/μL) on chiral hplc (30 μL injection volume, ChiralCel OD column (300 mm×4.6 mm), hexane-isopropanol (90:10) mobile phase, 1 mL/min, 30 min run, 260 nm detection]. (10aS)-7-Chloro-2-(trifluoroacetyl)-1,3,4,10,10a-pentahydropyrazino[1,2-a]indole was obtained as a colourless oil (15 mg): hplc 13.77 min [ChiralCel OD, above conditions, >99% ee].

(10aS) 7-Chloro-1,2,3,4,10,10a-hexahydropyrazino[1,2- ]indole hydrochloride

To a stirred solution of (10aS) 7-chloro-2-trifluoroacetyl)-1,3,4,10,10a-pentahydropyrazino[1,2-a]indole (~15 mg) in methanol (5 mL) was added potassium carbonate (~50 mg). After 16 h, the re was condensed, dissolved in a small amount of ethyl acetate-methanol (9:1), filtered and evaporated to afford the crude product. Purification by column chromatography [SiO$_2$; ethyl acetate-methanol-ammonium hydroxide (90:10:3)] afforded a colourless oil (5–10 mg). To a solution of the above oil in a few drops of acetone was added ethereal HCl (1 M; 0.15 mL) followed by ether (1 mL). Filtration and ether washing afforded the title compound (7.1 mg) as an off-white solid.

Example 8

(10aR) 7-Chloro-1,2,3,4,10,10a-hexahydropyrazino[1,2-a]indole hydrochloride

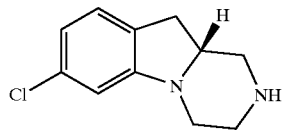

(10aR) 7-Chloro-2-(trifluoroacetyl)-1,2,4,10,10a-pentahydropyrazino[1,2-a]indole (RS) 7-Chloro-2-(trifluoroacetyl)-1,3,4,10,10a-pentahydropyrazino[1,2-a]indole was separated into the constituent enantiomers by repeat injecton of a solution in dichloromethane (~0.1 mg/μL) on chiral hplc (30 μL injection volume, ChiralCel OD column (300 mm×4.6 mm), hexane-isopropanol (90:10) mobile phase, 1 mL/min, 30 min run, 260 nm detection]. (10aR) 7-Chloro-2-(trifluoroacetyl)-1,3,4,10,10a-pentahydropyrazino[1,2-a]indole was obtained as a colourless oil (15 mg): hplc 18.60 min [ChiralCel OD, above conditions, >99% ee].

(10aR) 7-Chloro-1,2,3,4,10,10a-hexahydropyrazino[1,2a]indole hydrochloride

To a strired solution of (10aR) 7-chloro-3-(trifluoroacetyl)-1,2,4,4a,5-pentahydropyrazino[1,2-a] indole (~15 mg) in methanol (5 mL) was added potassium carbonate (~50 mg). After 16 h, the mixture was condensed, dissolved in a small amount of ethyl acetate-methanol (9:1), filtered and evaporated to afford the crude product. Purification by column chromatography [SiO$_2$; ethyl acetate-methanol-ammonium hydroxide (90:10:3)] afforded a colourless oil (5–10 mg). To a solution of the above oil in a few drops of acetone was added ethereal HCl (1 M; 0.15 mL) followed by ether (1 mL). Filtration and ether washing afforded the title compound (4.9 mg) as an off-white solid.

Example 9

(3R, 10aR) 7-Chloro-3-methyl-1,2,3,4,10,10a-hexahydropyrazino[1,2-a]indole hydrochloride

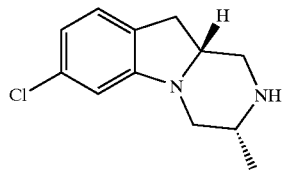

Methyl 6-chloro-indoline-2-carboxylate

To a stirred suspension-solution of ethyl 6-chloroindole-2-carboxylate (20.0 g, 89.4 mmol) in methanol (350 mL) under Ar was added magnesium turnings (21.7 g, 0.89 mol). After 10 min, the internal temperature had risen to 24° C. and effervescence was apparent. The mixture was cooled to 10–1S ° C. and was maintained for 1.5 h. After this time, the reaction mixture was allowed to warm to ambient temperature, and was stirred for 1 h. The mixture was poured onto saturated aqueous ammonium chloride solution (1 L), and ethyl acetate (300 mL) was added. After 1.5 h stirring, the layers were separated, and the aqueous layer was exacted with ethyl acetate (2×300 mL). The combined organic extracts were washed with brine (200 mL), dried (magnesium sulfate) and concentrated in vacuo to give a brown oil. Purification by flash column chromatography [SiO$_2$; ethyl acetate-heptane (1:3)] afforded the title compound (12.0 g, 63%) as an orange oil which crystallised on standing: IR $v_{max}$ (film)t/cm$^{-1}$ 3375, 2953, 2851, 1737, 1610, 1486, 1438, 1321, 1287, 1204, 1161, 1069, 1011, 948, 906, 846, 796, 794, 594 and 548; NMR $\delta_H$ (400 MHz; CDCl$_3$) 3.27 (1H, dd, J 16.0, 5.0 Hz), 3.34 (1H, ddd, J 16.0, 10.5, 1.0 Hz), 3.76 (3H, s), 4.40 (1H, dd, J 10.5, 5.0 Hz), 4.47 (H, br s), 6.68 (1H, br d, J 2 Hz), 6.69 (1H, dd, J 7.5, 2.0 Hz) and 6.96 (1H, d, J 7.5 Hz); hplc [Chiralcel OD; hexane-isopropanol (90:10); 1 mL/min; 260 nm] 50% (10.04 min) and 50% (11.61 min).

(2R,2'R) and (2S,2'R) Methyl 1-[2'-(tert-butoxycarbonylamino)propionyl]indoline-2-carboxylate To a stirred solution of Boc-d-alanine anhydride (3.64 g, 10 mmol) and N-methylmorpholine (1.3 mL, 12 mmol) in dichloromethane (50 mL) under Ar at 0° C. was added dropwise over 5 min a solution of methyl 6-chloro-indoline-2-carboxylate (1.06 g, 5 mmol) in dichloromethane (10 mL). The mixture was allowed to warm to ambient temperature, and was stirred for 3 days. The mixture was diluted with dichloromethane (50 mL) and was washed with water (50 mL), aqueous sodium hydrogen carbonate solution (2×50 mL), dilute hydrochloric acid (1N, 50 mL) and brine (50 mL). The organic phase was dried (magnesium sulfate) and concentrated in vacuo to afford the crude product as an amber oil (2.12 g). Purification by flash column chromatography [SiO$_2$; heptane-ethyl acetate (4:1)—(7:3)] gave the title compounds {[S,2'R (227 mg, 12%) as a colourless oil]: NMR $\delta_H$ (400 MHz; CDCl$_3$) 3.27 (1H, dd, J 16.0, 5.0 Hz), 3.34 (1H, ddd, J 16.0, 10.5, 1.0 Hz), 3.76 (3H, s), 4.40 (1H, dd, J 10.5, 5.0 Hz), 4.47 (1H, br s), 6.68 (1H, br d, J 2 Hz), 6.69 (1H, dd, J 7.5, 2.0 Hz) and 6.96 (1H, d, J 7.5 Hz); hplc [Supelcosil ABZ+; methanol-10 mM aqueous ammonium acetate solution (70:30); 1 mL/min; 230 nm] 92% (4.66 min)} and {[2R,2'R (675 mg, 35%) as a white solid]: mp 102.5–107.5° C.; hplc [Supelcosil ABZ+; methanol-10 mM aqueous ammonium acetate solution (70:30); 1 mL/min; 230 nm] 99% (4.57 min)].

(3R, 0aR) 7-Chloro-1,2,3,4,10,10a-hexahydro-3-methylpyrazino[1,2a-indole-1,4-dione To a stirred solution of (2R2'R) methyl 1-[2'-(tert-butoxycarbonylamino)propionyl]indoline-2-carboxylate (624 mg, 1.63 mmol) in methanol (20 mL) under Ar was added conc. hydrochloric acid (0.50 mL, 4.9 mmol.), and the resultant mixture was heated at reflux for 2 h. After allowing to cool, the solvent was removed in vacuo and the crude material was vigorously stirred for 1 h in a mixture of ethyl acetate (60 mL) and saturated aqueous sodium hydrogen carbonate solution (60 mL). The layers were separated and the aqueous phase was extracted with ethyl acetate (2×60 mL). The combined organic extracts were washed with water (60 mL) and brine (60 mL), dried (magnesium sulfate), filtered and concentrated under vacuum to give a light brown oil. Trituration with isopropyl ether afforded the title compound (369 mg, 89%) as a tan-coloured solid: mp 244–246.5° C.; NMR $\delta_H$ (400 MHz; DMSO-d$_6$) 1.34 (3H, d, J 6.5 Hz), 3.31 (1H, dd, J 16, 10 Hz), 3.37 (1H, dd, J 16, 10 Hz), 4.36 (1H, q, J 7 Hz), 5.09 (1H, t, J 10 Hz), 7.14 (1H, dd, J 8, 2 Hz), 7.35 (1H, d, J 8 Hz); hplc ]Supelcosil ABZ+; methanol-10 mM aqueous ammonium acetate solution (70:30); 1 mL/min; 230 nm] 91% (3.24 min).

(3R, 10aR) 7-Chloro-1,2,3,4,10,10a-hexahydro-3-methylpyrazino[1,2-a]indole hydrochloride To a stirred suspension of lithium aluminium hydride (95%; 220 mg, 5.5 mmol) in anhydrous ether (40 mL) under Ar was added (3R,10aR) 7-chloro-1,2,3,4,10,10a-hexahydro-3-methylpyrazino[1,2a]indole-1,4-dione (345 mg, 1.38 mmol). The mixture was heated at reflux for 8 h, then allowed to cool to ambient temperature. Water (0.22 mL) was added, followed by aqueous NaOH (15% w/v, 0.22 mL) then water (0.66 mL) and magnesium sulfate (~7 g) were added. The mixture was filtered and the filter-cake washed with ethyl acetate. The filtrate was concentrated in vacuo and purified by flash column chromatography [$SiO_2$; ethyl acetate-methanol-ammonium hydroxide (9:1:0)→(90:8:2)] to give a colourless oil (225 mg, 73%). A portion of the above oil (15 mg, 0.07 mmol) was dissolved in acetone (0.5 mL) and treated with ethereal HCl (1M; 0.21 mL, 0.21 mmol) followed by ether (3 mL). The resultant precipitate was filtered, washed with ether and dried to afford the title compound (16.3 mg, 93%) as a white solid: NMR $\delta_H$ (400 MHz; DMSO-$d_6$) 1.34 (3H, d, J 7 Hz), 2.67 (1H, dd, J, 15, 9 Hz), 3.05 (1H, dd, J, 15.5, 8 Hz), 3.15 (1H, m), 3.21 (1H, dd, J 13.5, 4 Hz), 3.27 (1H, m), 3.66 (1H, q, J 13 Hz), 3.75 (2H, m), 6.64 (1H, dd, J 8, 2 Hz), 6.68 (1H, d, J 2 Hz) and 7.08 (1H, d, J 8 Hz); hplc [Supelcosil ABZ+; methanol-10 mM aqueous ammonium acetate solution (80:20); 1 mL/min; 210 nm] 80% (2.45 min) and 14% (1.94 min, des-chloro material).

Example 10

(3R,10a) 7-Chloro-3-methyl-1,2,3,4,10,10a-hexahydropyrazino[1,2-a]indole hydrochloride

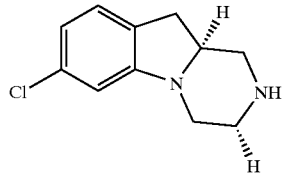

(3AR,10aS) 7-Chloro-1,2,3,4,10,10a-hexahydro-2-methylpyrazino[1,2-a]indole-1,4-dione To a stirred solution of (2S,2'R) methyl-1-[2'-(tert-butoxycarbonylamino)propionyl]indoline-2-carboxylate (205 mg, 0.54 mmol) in methanol (10 mL) under Ar was added conc. hydrochloric acid (0.16 mL, 1.6 mmol), and the resultant mixture was heated at reflux for 2 h. After allowing to cool, the solvent was removed in vacuo and the crude material was vigorously stirred for 1 h in a mixture of ethyl acetate (30 mL) and saturated aqueous sodium hydrogen carbonate solution (30 mL). The layers were separated and the aqueous phase was extracted with ethyl acetate (2×30 mL). The combined organic extracts were washed with water (30 mL) and brine (30 mL), dried (magnesium sulfate), filtered and concentrated under vacuum to give a light brown oil. Trituration with isopropyl ether afforded the title compound (104 mg, 77%) as a tan-coloured solid: mp 196–198° C.; NMR $\delta_H$ (400 MHz; $CDCl_3$) 1.40 (3H, d, J 7 Hz), 1.42 (9H, br. s), 3.30 (1H, d, J 16 Hz), 3.58 (dd, J 16, 5 Hz), 3.78 (3H, s), 4.36 (1H, t, J 7.5 Hz), 5.08 (1H, d, J 8 Hz), 5.71 (1H, d, J 10 Hz), 7.03 (1H, dd, J 8, 2 Hz), 7.08 (1H, d, J 8 Hz), 8.25 (1H, br. s); hplc [Supelcosil ABZ+; methanol-10 mM aqueous ammonium acetate solution (70:30); 1 mL/min; 230 mm] 98.6% (3.01 min).

(3R,10aS) 7-Chloro-1,2,3.4,10,10a-hexahydro-3-methylpyrazino[1,2-a]indole hydrochloride To a stirred suspension of lithium aluminium hydride (95%; 55 mg, 1.4 mmol) in anhydrous ether (15 mL) under Ar was added (3R,10aS)-7-chloro-1,2,3,4,10,10a-hexahydro-3-methylpyrazino[1,2-a]indole-1,4-dione (82 mg, 0.33 mmol). The mixture was heated at reflux for 18 h, then allowed to cool to ambient tempera . Water (0.06 mL) was added, followed by aqueous NaOH (15% w/v; 0.06 mL) then water (0.18 mL) and magnesium sulfate (2 g) were added. The mixture was filtered and the filter-cake washed with ethyl acetate. The filtrate was concentrated in vacuo and purification by flash column chromatography [$SiO_2$; ethyl acetate-methanol-ammonium hydroxide (9:1:0)→(90:8:2)] gave a colourless oil which crystallised on standing (53 mg, 74%). The oil was dissolved in acetone (0.5 mL) and treated with ethereal HCl (1M; 0.71 mL, 0.71 mmol) followed by ether (5 mL). The resultant precipitate was filtered, washed with ether and dried to afford the title compound (51 mg, 83%) as a white solid: mp 260° C. (dec); Found C, 55.63; H, 6.28; N, 10.61%. $C_{12}H_{16}Cl_2N_2$ requires: C, 55.61; H, 6.22; N, 10.80%.

Example 11

(3S,10aR) 7-Chloro-3-methyl-1,2,3,4,10,10a-hexahydropyrazino[1,2-a]indole hydrochloride

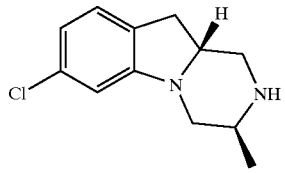

Methyl 6-chloro-indoline-2-carboxylate

To a stirred suspension-solution of ethyl 6-chloroindole-2-carboxylate (20.0 g, 89.4 mmol) in methanol (350 mL) under Ar was added magnesium turnings (21.7 g, 0.89 mol). After 10 min, the internal temperature had risen to 24° C. and effervescence was apparent. The mixture was to 10–15° C. and was maintained for 1.5 h. After this time, the reaction mixture was allowed to warm to ambient temperature, and was stirred for 1 h. The mixture was poured onto saturated aqueous ammonium chloride solution (1 L), and ethyl acetate (300 mL) was added. After 1.5 h sting, the layers were separated, and the aqueous layer was extracted with ethyl acetate (2×300 mL). The combined organic extracts were washed with brine (200 mL), dried (magnesium sulfate) and concentrated in vacuo to give a brown oil. Purification by flash column chromatography [$SiO_2$; ethyl acetate-heptane (1:3)] afforded the title compound (12.0 g, 63%) as an orange oil which crystallised on standing: IR $v_{max}$(film)/$cm^{-1}$ 3375, 2953, 2851, 1737, 1610, 1486, 1438, 1321, 1287, 1204, 1161, 1069, 1011, 948, 906, 846, 796, 794, 594 and 548; NMR $\delta_H$ (400 MHz; $CDCl_3$) 3.27 (1H, dd, J 16.0, 5.0 Hz), 3.34 (1H, ddd, J 16.0, 10.5, 1.0 Hz), 3.76 (3H, s), 4.40 (1H, dd, J 10.5, 5.0 Hz), 4.47 (1H, br s), 6.68 (1H, br d, J 2 Hz), 6.69 (1H, dd, J 7.5, 2.0 Hz) and 6.96 (1H, d, J 7.5 Hz); hplc [Chiralcel OD; hexane-isopropanol (90:10); 1 mL/min; 260 nm] 50% (10.04 min) and 5% (11.61 min).

(2R,2'S) and (2S,2'S) Methyl 1-[2'-(tert-butoxycarbonylamino)propionyl]indoline-2-carboxylate To a stirred solution of Boc-1-alanine anhydride (3.64 g, 10 mmol) and N-methylmorpholine (1.3 mL, 12 mmol) in dichloromethane (50 mL) under Ar at 0° C. was added dropwise over 5 min a solution of methyl 6-chloro-indoline-2-carboxylate (1.06 g, 5 mmol) in dichloromethane (10 mL). The mixture was allowed to warm to ambient temperature, and was stirred for 8 days. The mixture was diluted with dichloromethane (50 mL) and was washed with water (50 mL), aqueous sodium hydrogen carbonate solution (2×50 mL), dilute hydrochloric acid (1N, 50 mL) and brine (50 mL). The organic phase was dried (magnesium sulfate) and concentrated in vacuo to afford the crude product as an amber oil (2.12 g). Purification by flash column [SiO$_2$; heptane-ethyl acetate (4:1)] gave the title compounds {[2R, 2'S (226 mg, 12%, 98% ee) as a colourless oil]: NM $\delta_H$ (400 MHz; CDCl$_3$) 1.35–1.45 (12H, m), 3.30 (1H, d, J 16.0 Hz), 3.58 (1H, dd, J 16.0, 10.5 Hz), 3.78 (3H, s), 4.30–4.40 (1H, m), 5.05 (1H, br d, J 9 Hz), 5.70 (1H, d, J 10.5 Hz), 7.04 (1H, dd, J 8.0, 2.0 Hz), 7.08 (1H, d, J 8.0 Hz) and 8.25 (1H, br s); hplc [ChiralCel OD; hexane-isopropanol (90:10); 1 mL/min; 230 nm]99% (6.57 min) and 1% (9.85 min, 2S, 2'R); [Supelcosil ABZ+; methanol-10 mM aqueous ammonium acetate solution (80:20); 1 mL/min; 230 mm] 91% (2.94 min)} and {[2S,2'S (610 mg, 32%, 94% ee) as a white solid]: mp 107–108.5° C.; hplc [Chiralcel OD; hexane-isopropanol (90:10); 1 mL/min; 230 m] 97% (11.50 min) and 3% (17.37 min 2R,2'R); [Supelcosil ABZ+; methanol-10 mM aqueous ammonium acetate solution (80:20); 1 mL/min; 230 nm] 98.7% (2.88 min); Found C, 56.77; H, 6.09, N, 7.27%. C$_{18}$H$_{23}$ClN$_2$O$_5$ requires: C, 56.47; H, 6.06; N, 731%}.

(3S,10aR) 7-Chloro-1,2,3,4,10,10a-hexahydro-3-methylpyrazino[1,2-a]indole-1,4dione To a stirred solution of (2R2'S) methyl-1-[2'-(tert-butoxycarbonylamino)propionyl]indoline-2carboxylate (207 mg, 0.54 mmol) in methanol (10 mL) under Ar was added conc. hydrochloric acid (0.16 mL, 1.6 mmol), and the resultant mixture was heated at reflux for 2 h. After allowing to cool, the solvent was removed in vacua and the crude material was vigorously stirred for 1 h in a mixture of ethyl acetate (30 mL) and saturated aqueous sodium hydrogen carbonate solution (30 mL). The layers were separated and the aqueous phase was extracted with ethyl acetate (2×30 mL). The combined organic extracts were washed with water (30 mL) and brine (30 mL), dried (magnesium sulfate), filtered and concentrated under vacuum to give a light brown oil. Trituration with isopropyl ether afforded the title compound (99 mg, 73%) as a tan-coloured solid: mp 190–193.5° C.; NMR $\delta_H$ (400 MHz; DMSO-d$_6$) 1.43 (1H, d, J 7.0 Hz), 3.27 (2H, d, J 10.0 Hz), 3.96 (1H, qd, J 7.0, 4.0 Hz), 5.16 (1H, t, J 10.0 Hz), 7.15 (1H, dd, J 8.0, 2.0 Hz), 7.34 (l1H, d, J 8.0 Hz), 7.94 (1H, d, J 2.0 Hz) and 8.50 (1H, br d, J 4 Hz); hplc [Supelcosil ABZ+; methanol-10 mM aqueous ammonium acetate solution (80:20); 1 mL/min; 230 nm] 97.8% (2.48 min).

(3S,10aR) 7-Chloro-1,2,3,4,10,10a-hexahydro-3-methylpyrazino[1,2-a]indole hydrochloride To a stirred suspension of lithium aluminium hydride (95%; 55 mg, 1.4 mmol) in anhydrous ether (15 mL) under Ar was added (3S,10aR) 7-chloro-1,2,3,4,10,10a-hexahydro-3-methylpyrazino[1,2-a]indole-1,4-dione (83 mg, 0.33 mmol). The mixture was heated at reflux for 18 h, then allowed to cool to ambient temperature. Water (0.06 mL) was added, followed by aqueous NaOH (15% w/v; 0.06 mL) then water (0.18 mL) and magnesium sulfate (2 g) was added. The mixture was filtered and the filter-cake washed with ethyl acetate. The filtrate was concentrated in vacuo and purification by flash column chromatography [SiO$_2$; ethyl acetate-methanol-ammonium hydroxide (9:1:0)→ (90:8:2)] gave a colourless oil which crystallised on standing (68 mg, 92%). The oil was dissolved in acetone (0.5 mL) and treated with ethereal HCl (1M; 0.81 mL, 0.81 mmol) followed by ether (5 mL). The resultant precipitate was filtered, washed with ether and dried to afford the title compound (62 mg, 78%) as a white solid: mp 265° C. (dec); Found C, 55.66; H, 62.8; N, 10.72%. C$_{12}$H$_{16}$Cl$_2$N$_2$ requires: C, 55.61; H, 6.22; N, 10.80%.

Example 12

(RS) 7-Chloro-8-fluoro-1,2,3,4,10,10a-hexahydropyrazino[1,2-a]indole hemifumarate

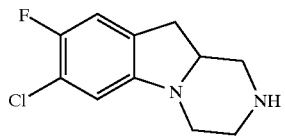

1-(6-Chloro-5-fluoroindol-1-yl)-2-ethylamine

Tetra-n-butylammonium hydrogensulfate (0.1 g, 0.33 mmol), powdered sodium hydroxide (1.3 g, 33 mmol) and 6-chloro-5-fluoroindole (1.4 g, 8.3 mmol) were stirred at room tempera in acetonitrile (40 mL) for 1 h. 2-Chloroethylamine hydrochloride (1.45 g, 12.5 mmol) was then added in 1 portion and the reaction was heated to reflux and stirred for 36 h. After allowing to cool to room temperature the mixture was poured into water (100 mL) and extracted with ethyl acetate (3×70 mL). The combined organic extracts were washed with brine (1×100 mL), dried (magnesium sulfate), filtered and the solvent removed under vacuo to leave a crude oil. The oil was purified by flash column chromatography [SiO$_2$; ethyl acetate-methanol-ammonium hydroxide, (90:9:1)] to give the product as an orange oil (1.4 g, 80%). IR $v_{max}$ (film)/cm$^{-1}$ 3377, 3104, 2937, 2868, 1675, 1568, 1505, 1479, 1449, 1400, 1357, 1327, 1291, 1236, 1143, 1090, 1030, 994, 862, 817, 753, 717, 698, 678, 646, 633, 596 and 579; NMR $\delta_H$ (400 MHz; DMSO-d$_6$) 7.79 (1H, d, J 7 Hz), 7.51 (1H, d, J 10 Hz), 7.50 (1H, d, J 3.5 Hz), 6.46 (1H, m), 4.13 (2H, t, J 6.3 Hz), 2.86 (2H, t, J 6.3 Hz), 1.52 (1H, br. s).

7-Chloro-8-fluoro-1,2,3,4-tetrahydropyrazino[1,2-a]indole

Paraformaldehyde (0.95 g, 30 mmol) was added in 1 portion to a stirred solution of 1-(6-chloro-7-fluoroindol-1-yl)-2-ethylamine (1.3 g, 6.1 mmol) and magnesium sulfate (1.5 g) in dichloromethane (15 mL) at room temperature under Ar. The reaction was stirred at room temperature for 4 h then filtered. The filter-cake was washed with dichloromethane (50 mL) and the filtrate was concentrated under vacuum to leave a crude oil. The oil was dissolved in dichloromethane (10 mL) and trifluoroacetic acid (2 mL) was added. The reaction was stirred at room temperature under Ar for 10 min then basified by pouring into saturated aqueous sodium hydrogen carbonate solution (100 mL). The mixture was extracted with ethyl acetate (3×80 mL) and the combined organic extracts were washed with brine (1×80 mL), dried (magnesium sulfate), filtered and the solvent removed under vacuum to leave a crude oil. The oil was purified by flash column chromatography [SO$_2$; ethyl acetate-methanol-ammonium hydroxide (9:1:0)—(90:9:1)] to give the product as a yellow oil that crystallised on standing (0.32 g, 23%). NMR $\delta_H$ (400 MHz; CDCl$_3$) 7.25–727 (2H, m), 6.14 (1H, s), 4.20 (2H, s), 3.95 (2H, t, J 5.5 Hz), 3.35 (2H, t, J 5.5 Hz).

(RS) 7-Chloro-8-fluoro-1,2,3,4,10,10a]-hexahydropyrazino[1,2-a]indole hemifumarate Sodium cyanoborohydride (95%, 0.29 g, 4.4 mmol) was added in 1 portion to a stirred solution of 7-chloro-8-fluoro-1,2,3,4-tetrahydropyrazino[1,2-a]indole (0.3 g, 1.3 mmol) in acetic acid (10 mL) 10° C. under Ar. The reaction was stirred at 10° C. for 10 min then allowed to warm to room temperature and stirred for 18 h. The mixture was basified by pouring into saturated aqueous sodium hydrogen carbonate solution (100 mL) and extracted with ethyl acetate (3×50 mL). The combined organic extracts were washed with brine (1×50 mL), dried (magnesium sulfate), filtered and the solvent removed under vacuum to leave a crude oil. The oil was purified by flash column chromatography [SiO$_2$; ethyl acetate-methanol-ammonium hydroxide, (90:10:0)→(90:9:1)] to give an oil (0.09 g). The oil was dissolved in boiling 2-propanol (2 mL) and fumaric acid (1 eq) was added. The solution was allowed to cool and the resulting precipitate was filtered off, washed with ether and dried to give the product as a white solid (0–07 g, 19%). mp 195–197° C. Found: C, 54.55; H, 5.07; N, 9.45%. C$_{11}$H$_{12}$ClFN$_2$.0.5 C$_4$H$_4$O$_4$ requires: C, 54.84; H, 4.96; N, 9.83%. IR $v_{max}$ (Nujol)/cm$^{-1}$ 4330, 4257, 3387, 2924, 2854, 2673, 2363, 1647, 1613, 1600, 1509, 1485, 1462, 1415, 1378, 1357, 1319, 1285, 1264, 1230, 1209, 1195, 1148, 1081, 1040, 1001, 955, 877, 858, 838, 820, 806, 766, 750, 722, 688, 677, 624, 595, 574, 516, 489 and 456; NMR $\delta_H$ (400 MHz; DMSO-d$_6$) 7.30 (1H, d, J 9 Hz), 6.82 (1H, d, J 5.9 Hz), 6.69 (1H, s), 3.73–3.80 (2H, m), 3.60.3.70 (2H, m), 2.98–3.06 (1H, m), 2.84–2.90 (1H, m).

Example 13

(RS) 7-(Methylthio)-1,2,3,4,10,10a-hexahydropyrazino[1,2-a]indole fumarate

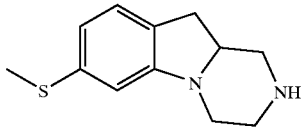

Ethyl 4-iodo-2-nitrophenyl acetate, potassium salt

Potassium tert-butoxide (16.0 g, 0.14 mol) was added portionwise to ethanol (25 mL) at 0° C. under Ar in one portion. The reaction was stirred for 10 min then diluted with ether (300 mL) and allowed to warm to room temperature. Diethyl oxalate (19.4 mL, 0.14 mol) was added in one portion followed by immediate addition of 4-iodo-2-nitrotoluene (25 g, 95 mmol). The reaction was heated to reflux and stirred for 4 h. After allowing to cool to room temperature the mixture was cooled to 4° C. and aged for 40 h. The mixture was filtered and the filter-cake washed with ether and dried to give the product as a red solid (22.5 g, 57%). IR $v_{max}$ (Nujol)/cm$^{-1}$ 3428, 2925, 2855, 2728, 1731, 1648, 1589, 1550, 1529, 1466, 1378, 1327, 1290, 1205, 1137, 1110, 1066, 1024, 926, 900, 870, 830, 774, 723, 694, 626, 565, 536 and 500; NMR $\delta_H$ (400 MHz; DMSO-d$_6$) 9.20 (1H, d, J 9 Hz), 8.03 (1H, d, J 2 Hz), 7.44 (1H, dd, J 9 Hz, 2 Hz), 6.52 (1H, s), 4.07 (2H, q, J 7 Hz), 1.22 (3H, t, J 7 Hz).

Ethyl 6-iodoindole-2-carboxylate

Iron powder (5.34 g, 95 mmol) was added in 1 portion to a stirred solution of ethyl 4-iodo-2-nitrophenyl acetate potassium salt (12.8 g, 32 mmol), in acetic acid (100 mL) at room temperature under Ar. The reaction was then heated to 90° C. and stirred for 45 min. After allowing to cool to room temperature the mixture was cautiously poured into stirred sodium hydrogen carbonate (25 g) in saturated aqueous sodium hydrogen carbonate solution (200 mL) and ethyl acetate (200 mL). The mixture was filtered through celite and the filtrate partitioned. The aqueous layer was extracted with ethyl acetate (2×200 mL) and the combined organic extracts were dried (magnesium sulfate), filtered and the solvent removed under vacuum to leave a crude solid (7.0 g, 70%). IR $v_{max}$ (Nujol)/cm$^{-1}$ 3319, 2924, 2855, 1800, 1695, 1609, 1568, 1520, 1482, 1463, 1421, 1372, 1316, 1238, 1223, 1206, 1131, 1106, 1040, 1023, 974, 942, 904, 868, 856, 822, 792, 766, 736, 658, 584 and 548; NMR $\delta_H$ (400 MHz; DMSO-d$_6$) 11.98 (1H, br. s), 7.83 (1H, s), 7.38–7.52 (1H, m), 7.16 (1H, m), 4.33 (2H, q, J 7Hz), 1.33 (3H, t, J 7 Hz).

Ethyl 1-(cyanomethyl)iodoindole-2-carboxylate

A solution of ethyl 6-iodoindole-2-carboxylate (7.0 g, 22 mmol) in DMF (25 mL) was added dropwise over 15 min to a stirred suspension of sodium hydride (60, 1.36 g, 34 mmol) in DMF (50 mL) at 0° C. under Ar. The reaction was stirred at 0° C. for 45 min then chloroacetonitrile (2.85 mL, 45 mmol) was added in one portion. The reaction was then heated to 75° C. and stirred for one h. After allowing to cool to room temperate the mixture was poured into water (300 mL) and extracted with ethyl acetate (3×200 mL). The combined organic extracts were washed with brine (1×200 ml), dried (magnesium sulfate), filtered and the solvent removed under vacuum to give the product (1.8 & 23%). IR $v_{max}$ (Nujol)/cm$^{-1}$ 2924, 2854, 1895, 1703, 1601, 1527, 1464, 1446, 1426, 1398, 1377, 1366, 1334, 1308, 1261, 1204, 1148, 1135, 1119, 1103, 1048, 1024, 989, 949, 904, 894, 871, 842, 833, 800, 786, 762, 736, 654, 612, 584 and 471; NMR $\delta_H$ (400 MHz; CDCl$_3$) 7.79 (1H, s), 7.51 (1H, d, J 8.6 Hz), 7.42 (1H, d, J 8.6 Hz), 7.32 (1H, s), 5.54 (2H, s), 4.37 (2H, q, J 7 Hz), 1.39 (3H, t, J 7 Hz).

7-Iodo-1,2,3,4-tetrahydropyrazino[2-a]indole

Ethyl 1-(cyanomethyl)-6-iodoindole-2-carboxylate (1.77 g, 5 mmol) was added portion-wise over 2 min to a stirred suspension of lithium aluminium hydride (0.48 g, 13 mmol) in ether (50 mL) at 0° C. under Ar. The reaction was then heated to reflux and stirred for 18 h. After allowing to cool to room temperature the mixture was poured into a mixture of saturated aqueous potassium sodium tartrate solution (150 mL) and ethyl acetate (100 mL). The mixture was filtered through celite and the biphasic filtrate was separated. The aqueous layer was extracted with ethyl acetate (2×50 mL) and the combined organic extracts were washed with brine (1×75 mL), dried (magnesium sulfate), filtered and the solvent removed under vacuum to leave a crude oil. The oil was purified by flash column chromatography [SiO$_2$; ethyl acetate-methanol, (9:1)] to give the product as a yellow solid (0.47 g, 32%, contains 15% of de-iodinated material). IR $v_{max}$ (Nujol)/cm$^{-1}$ 3306, 2924, 2855, 1882, 1735, 1664, 1598, 1527, 1460, 1410, 1378, 1356, 1338, 1322, 1298, 1282, 1246, 1218, 1202, 1170, 1143, 1116, 1045, 1001, 984, 943, 919, 876, 840, 814, 773, 740, 698, 637, 617, 589, 522 and 488; NMR $\delta_H$ (400 MHz; CDCl$_3$) 7.60 (1H, m), 7.35–7.37 (1H, m), 7.28 (1H, d, J 7.8 Hz), 6.15 (1H, m), 4.19 (2H, m), 3.94 (2H, t, J 5.8 Hz), 3.33 (2H, t, J 5.8 Hz), 1.79 (1H, br. s).

(RS) 7-Iodo-1,2,3,4,10,10a-hexahydropyrazino[1,2-a]indole

Sodium cyanoborohydride (95%, 1.6 g, 24 mmol) was added over 3 mm to a stirred solution of 7-iodo-1,2,3,4-tetrahydropyrazino-[1,2-a]indole (2.2 g, 7.4 mmol) in acetic acid (50 mL) at 10° C. under Ar. After complete addition the reaction was allowed to warm to room temperature and stirred for 18 h. The mixture was cautiously poured into a mixture of saturated aqueous sodium hydrogen carbonate solution (150 mL) and ethyl acetate (100 mL). The mixture was partitioned and the aqueous layer was extracted with ethyl acetate (2×100 mL). The combined organic extracts were washed with brine (1×100 mL), dried (magnesium sulfate), filtered and the solvent removed under vacuum to leave a crude oil. The oil was purified by flash column chromatography [SiO$_2$; ethyl acetate-methanol-ammonium hydroxide, (90:9:1)] to give the product as a yellow oil (1.74 g, 79%) which was used immediately.

(RS) 2-tert-Butoxycarbonyl-7-iodo-1,2,3,4,10,10a-hexahydropyrazino[1,2-a]indole

Di-tert-butyl-dicarbonate (2.53 g, 12 mmol) was added to a stirred solution of 7-iodo-1,2,3,4,10,10a-hexahydropyrazino[1,2-a]indole in dichloromethane (50 mL) at 0° C. under Ar. The reaction was allowed to warm to room temperature and stirred for 2 h. Another portion of di-tert-butyl-dicarbonate (2 g) was added and the reaction was stirred at room temperature for 1 h. The mixture was washed with water (1×50 mL) and brine (1×50 mL). The combined aqueous layers were extracted with dichloromethane (1×50 mL) and the combined organic layers were dried (magnesium sulfate), filtered and the solvent removed under vacuum to leave a crude oil. The oil was purified by flash column chromatography [SiO$_2$; ethyl acetate-heptane (9:1)] to give the product as a yellow oil (0.2 g, 9%). IR $v_{max}$ (film)/cm$^{-1}$ 3510, 2975, 2927, 2855, 1737, 1692, 1601, 1573, 1479, 1457, 1417, 1365, 1306, 1263, 1240, 1214, 1163, 1127, 1048, 1024, 996, 964, 901, 879, 831, 805, 789, 770, 749, 715, 644, 615, 591, 561 and 514; NMR $\delta_H$ (400 MHz; CDCl$_3$) 6.97 (1H, m), 6.79 (1H, d, J 7.5 Hz), 6.73 (1H, m), 3.41–3.44 (3H, m), 2.86–2.97 (5H, m), 2.49–2.55 (1H, m), 1.47 (9H, s).

(RS) 2-tert-Butoxycarbonyl-7-(methylthio)-1,2,3,4,10,10a-hexahydropyrazino[1,2-a]indole Triphenylphosphine (28 mg) was added in 1 portion to a stirred solution of palladium(II) acetate (6 mg) in THF (2.5 mL) at room temperate under Ar. After stirring at room temperature under Ar for 10 min a solution of 2-tert-butoxycarbonyl-7-iodo-1,2,3,4,10,10a-hexahydropyrazino[1,2-a]indole (0.20 g, 0.5 mmol) in THF (5 mL) was added. The reaction was stirred at room temperature for 10 min then a solution of (methylthio)tributyltin (035 g, 1 mmol) in THF (2.5 mL) was added. The reaction was heated to reflux and stirred for 2 days. After allowing to cool to room temperature the mixture was poured into water (50 mL) and extracted. with ethyl acetate (3×30 mL). The combined organic extracts were washed with brine (r×50 mL), dried (magnesium sulfate), filtered and the solvent removed under vacuum to leave a crude oil. The oil was purified by flash column chromatography [SiO$_2$; ethyl acetate-heptane (1:20)] to give the product as a yellow oil (0.08 g, 50%). NMR $\delta_H$ (400 MHz; CDCl$_3$) 6.97 (1H, d, J 7.5 Hz), 6.56 (1H, dd, J 7.5, 1.5 Hz), 6.36 (1H, d, J 11 Hz), 3.94–4.26 (2H, m), 3.35–3.49 (2H, m), 2.78–2.96 (41, m), 2.49–2.55 (1H, m), 2.44 (311, s), 1.46 (9H, s).

(RS) 7-(Methylthio)-1,2,3,4,10,10a-hexahydropyrazino[1,2-]indole fumarate

Trifluoroacetic acid (1 mL) was added to a stirred solution of 2-tert-butoxycarbonyl-7-(methylthio)-1,2,3,4,10,10a-hexahydropyrazino[1,2, -a]dole (70 mg, 0.2 mmol) in dichloromethane (5 mL) at room temperature under Ar. The reaction was stirred at room temperature for 1 h then poured into sated aqueous sodium hydrogen carbonate solution (50 mL) and extracted with dichloromethane (3×30 mL). The combined organic extracts. were washed with brine (1×30 mL), dried (magnesium sulfate), filtered and the solvent removed under vacuum to leave a crude oil. The oil was dissolved in 2-propanol (5 mL) and heated to reflux. Fumaric acid (1 eq) was added and the solution was cooled to room temperature. The emerging precipitate was filtered, washed with ether and dried to give the product as a white solid (40 mg, 54%). mp 196–198° C. Found. C, 56.50; H, 5.89; N, 8.15%. $C_{12}H_{16}N_2S$. 1.1 $C_4O_4$ requires: C, 56.60; H, 5.91; N, 8.05%. IR $v_{max}$ (Nujol)/cm$^{-1}$ 3595, 3188, 2925, 2854, 2457, 1696, 1585, 1485, 1486, 1461, 1402, 1377, 1345, 1317, 1279, 1230, 1179, 1154, 1129, 1066, 1058, 1005, 996, 972, 919, 987, 868, 835, 797, 722, 644, 606, 547 and 482: NMR $\delta_H$ (400 MHz; DMSO-d$_6$) 6.99 (1H, d, J 7.5 Hz), 6.52 (2H, s), 6.47–6.51 (2H, m), 3.69–3.72 (1H, m), 3.503.62 (2H, m), 3.05–3.20 (3H, m), 2.91–3.02 (2H, m), 2.65–2.80 (2H, m), 2.43 (3H, s).

What is claimed is:

1. A pharmaceutical composition comprising a chemical compound of formula (I):

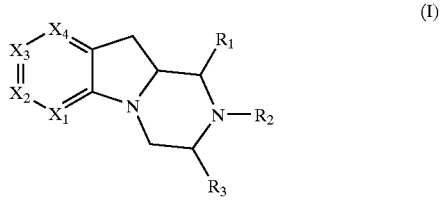

wherein:
R$_1$ to R$_3$ are independently selected from hydrogen and lower alkyl;
X$_1$ is C—R$_4$:
X$_2$ is C—R$_5$;
X$_3$ is C—R$_6$;
X$_4$ is C—R$_7$;
R$_4$, R$_5$ and R$_7$ are independently selected from hydrogen, halogen, alkyl, haloalkyl, haloalkoxy and alkylthio; and
R$_6$ is selected from hydrogen, halogen, alkyl, haloalkyl and alkylthio,
with the proviso that R$_4$ to R$_7$ are not all selected as hydrogen,
or a pharmaceutically acceptable salt, or addition compound thereof; in combination with a pharmaceutically acceptable carrier or excipient.

2. A pharmaceutical composition according to claim 1, wherein R$_1$ is selected from hydrogen and methyl.

3. A pharmaceutical composition according to claim 1, wherein R$_2$ is hydrogen.

4. A pharmaceutical composition according to claim 1, wherein R$_3$ is selected from hydrogen and methyl.

5. A pharmaceutical composition according to claim 1, wherein two of R$_4$, R$_5$, R$_6$ and R$_7$ are hydrogen.

6. A pharmaceutical composition according to claim 5, wherein R$_4$ and R$_6$ are hydrogen.

7. A pharmaceutical composition according to claim 1, wherein two of R$_4$, R$_5$, R$_6$ and R$_7$ are independently selected from hydrogen, chlorine, fluorine, trifluoromethyl and bromine.

8. A pharmaceutical composition according to claim 1, wherein three of R$_4$, R$_5$, R$_6$ and R$_7$ are hydrogen.

9. A pharmaceutical composition according to claim 8, wherein R$_4$, R$_6$ and R$_7$ are hydrogen.

10. A pharmaceutical composition according to claim 1, wherein R₄ is hydrogen.

11. A pharmaceutical composition according to claim 1, wherein R₅ is halogen.

12. A pharmaceutical composition according to claim 1, wherein R₆ is hydrogen.

13. A pharmaceutical composition according to claim 1, wherein R₇ is halogen.

14. A pharmaceutical composition according to claim 1 wherein the compound of formula (I) is selected from:
- (RS) 7-chloro-1,2,3,4,10,10a-hexahydropyrazino[1,2-a]indole,
- (R5) 9-chloro-1,2,3,4,10,10a-hexahydropyrazino[1,2-a]indole,
- (RS) 7-chloro-8-methyl-1,2,3,4,10,10a-hexahydropyrazino[1,2-a]indole,
- (10aR) 7-chloro-1,2,3,4,10,10a-hexahydropyrazino[1,2-a]indole,
- (RS) 7-bromo-1,2,3,4,10,10a-hexahydropyrazino[1,2-a]indole,
- (3S, 10aR) 8-chloro-2-methyl-1,2,3,4,10,10a-hexahydropyrazino[1,2-a]indole,
- (10aR) 8-chloro-1,2,3,4,10,10a-hexahydropyrazino[1,2-a]indole and
- (3S, 10aR) 8-chloro-2-methyl-1,2,3,4,10,10a-hexahydropyrazino[1,2-a]indole.

15. A method of treatment of obesity, comprising administering to a patient in need of such treatment an effective dose of a compound of formula (I) as set out in claim 1.

16. A process for the preparation of a compound of formula (I):

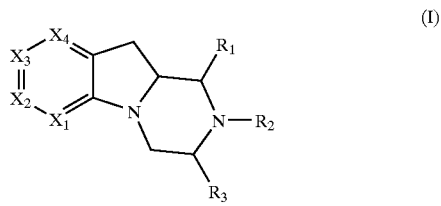

wherein:
- R₁ to R₃ are independently selected from hydrogen and lower alkyl;
- X₁ is C—R₄;
- X₂ is C—R₅;
- X₃ is C—R₆;
- X₄ is C—R₇;
- R₄, R₅ and R₇ are independently selected from hydrogen, halogen, hydroxy, alkyl, aryl, alkoxy, aryloxy, alkoyl, aryloyl, alkylthio, arylthio, alkylsulfoxyl, arylsulfoxyl, alkylsulfonyl, arylsulfonyl, amino, alkylamino, dialkylamino, nitro, cyano, carboalkoxy, carboaryloxy and carboxy; and
- R is selected from hydrogen, halogen, alkyl, aryl, aryloxy, alkylthio, arylthio, alkylsulfoxyl, arylsulfoxyl, alkylsulfonyl, arylsulfonyl, amino, alkylamino, dialkylamino and cyano;
- with the proviso that R₄ to R₇ are not all selected as hydrogen, said process comprising the steps of:
(i) treating a compound of formula (IX) with an aldehyde of formula R, CHO and then exposing to acid to obtain a compound of formula (X), wherein X₁, X₂, X₃, X₄, R₂ and R₃ are as described in claim 1, and

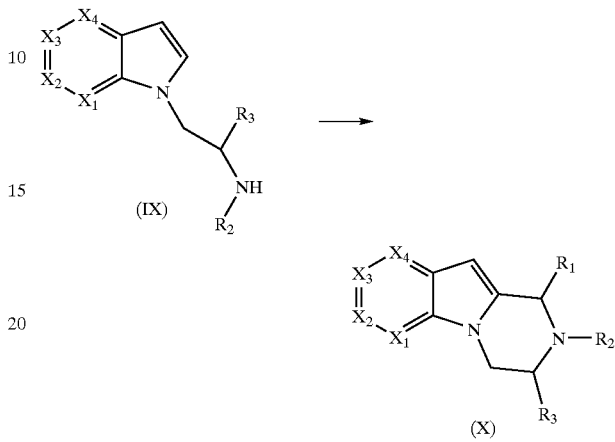

(ii) reduction of a compound of formula (X).

17. A process according to claim 16 with the proviso that where R₁ to R₃ and three of R₄ to R₇ are selected from hydrogen, the remaining R₄ to R₇ is not selected from methoxy.

18. A process for the preparation of a compound according to claim 1, said process comprising the steps of:
(i) treating a compound of formula (IX) with an aldehyde of formula R, CHO and then exposing to acid to obtain a compound of formula (X), wherein X₁, X₂, X₃, X₄, R₂ and R₃ are as described in claim 1, and

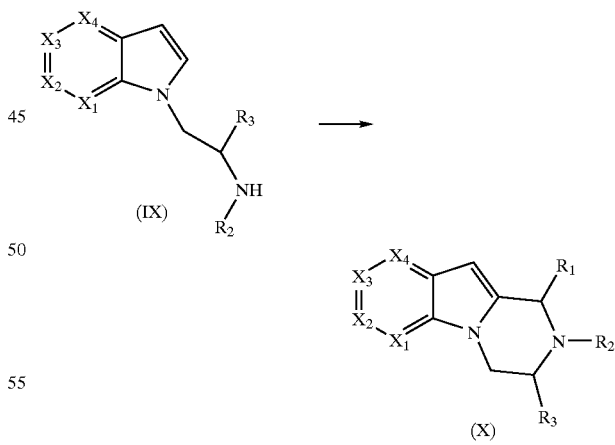

(ii) reduction of a compound of formula (X).

* * * * *